United States Patent
Sui et al.

(10) Patent No.: US 10,544,205 B2
(45) Date of Patent: Jan. 28, 2020

(54) ANTI-PRE-S1 HBV ANTIBODIES

(71) Applicant: HUAHUI HEALTH LTD., Beijing (CN)

(72) Inventors: Jianhua Sui, Waltham, MA (US); Dan Li, Beijing (CN); Wenhui Li, Beijing (CN)

(73) Assignee: HUAHUI HEALTH LTD., Changping (CN)

( * ) Notice: Subject to any disclaimer, the term of this patent is extended or adjusted under 35 U.S.C. 154(b) by 0 days.

(21) Appl. No.: 15/864,494

(22) Filed: Jan. 8, 2018

(65) Prior Publication Data

US 2018/0148496 A1   May 31, 2018

Related U.S. Application Data

(63) Continuation of application No. 15/566,555, filed as application No. PCT/CN2016/082985 on May 23, 2016, now abandoned.

(30) Foreign Application Priority Data

May 22, 2015   (WO) ................ PCT/CN2015/079534

(51) Int. Cl.
*C07K 16/08* (2006.01)
*A61P 31/20* (2006.01)
*A61K 39/00* (2006.01)

(52) U.S. Cl.
CPC ............ *C07K 16/082* (2013.01); *A61P 31/20* (2018.01); *A61K 2039/505* (2013.01); *C07K 2317/21* (2013.01); *C07K 2317/34* (2013.01); *C07K 2317/56* (2013.01); *C07K 2317/565* (2013.01); *C07K 2317/622* (2013.01); *C07K 2317/732* (2013.01); *C07K 2317/76* (2013.01)

(58) Field of Classification Search
None
See application file for complete search history.

(56) References Cited

U.S. PATENT DOCUMENTS

| 7,115,723 B1 | 10/2006 | Hong et al. |
| 7,892,754 B2 | 2/2011 | Gripon et al. |
| 2018/0094047 A1 | 4/2018 | Sui et al. |

FOREIGN PATENT DOCUMENTS

| EP | 0456215 A | 11/1991 | |
| WO | WO 2000/31141 | * 11/1999 | ............. C07K 16/28 |
| WO | WO 2000/031141 A1 | 6/2000 | |
| WO | WO 2013/159243 A1 | 10/2013 | |
| WO | WO 2016/188386 A1 | 12/2016 | |

OTHER PUBLICATIONS

Li et al. (eLife Sciences, 2017 p. 1-30).*
International Preliminary Report on Patentability for International Application No. PCT/CN2016/082985, dated Nov. 28, 2017, 4 pages.
International Search Report and Written Opinion for International Application No. PCT/CN2016/082985, dated Jul. 13, 2016, 7 pages.
Chi, et al., "Broadly neutralizing anti-hepatitis B virus antibody reveals a complementarity determining region H3 lid-opening mechanism." PNAS (2007); 104(22): 9230-9235.
Ryu, et al., "Short Communication: Mouse Monoclonal Antibodies to Hepatitis B Virus PreS1 Produced After Immunization with Recombinant PreS1 Peptide." Hybridoma (2000); 19(2): 185-189.
Sureau, et al., "Production of infectious hepatitis delta virus in vitro and neutralization with antibodies directed against hepatitis B virus pre-S antigens." J. Virol. (1992); 66(2): 1241-1245.
Watashi, et al., "NTCP and Beyond: Opening the Door to Unveil Hepatitis B Virus Entry." Int. J. Mol. Sci. (2014); 15(2): 2892-2905.
Hong et al., "In vivo neutralization of hepatitis B virus infection by an anti-preS1 humanized antibody in chimpanzees," Virology. (2004) 318(1):134-41.
Küttner, et al., "Characterization of neutralizing anti-pre-S1 and anti-pre-S2 (HBV) monoclonal antibodies and their fragments." Molecular Immunology (1999); 36 (10): 669-683.
Maeng, C-Y, et al., "Fine Mapping of Virus-Neutralizing Epitopes on Hepatitis B Virus PreS1." Virology (2000); 270: 9-16.
Niedre-Otomere, et al., "Recombinant Semliki Forest virus vectors encoding hepatitis B virus small surface and pre-S1 antigens induce broadly reactive neutralizing antibodies." Journal of Viral Hepatitis (2012); 19 (9): 664-673.
Partial Supplementary European Search Report for European Patent Application No. 16799274.2, dated Jul. 17, 2018, 14 pages.
Ryu, et al., "A humanized antibody with specificity for hepatitis B surface antigen." Human Antibodies and Hybridomas (1996); 7 (3): 113-122.
Ryu, et al., "In Vitro Neutralization of Hepatitis B Virus by Monoclonal Antibodies Against the Viral Surface Antigen." Journal of Medical Virology (1997); 52 (2): 226-233.

* cited by examiner

*Primary Examiner* — Agnieszka Boesen
(74) *Attorney, Agent, or Firm* — Cooley LLP

(57) ABSTRACT

Provided are human antibodies that specifically bind to HBV Pre-S1 domain ligand and inhibit HBV or HDV infection, antibodies binding to a set of amino acid residues that are critical for viral receptor engagement, and uses of these antibodies to prevent, or treat or diagnose HBV or HDV infection.

8 Claims, 1 Drawing Sheet
Specification includes a Sequence Listing.

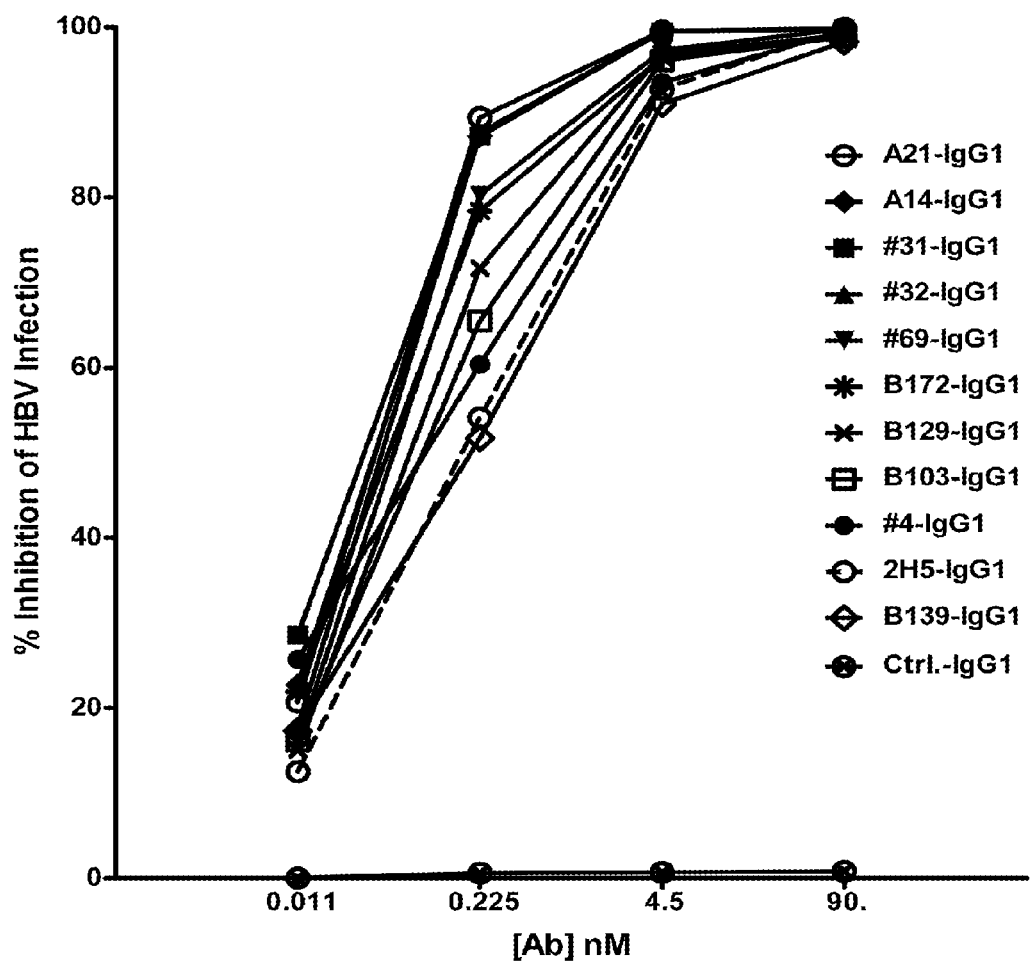

SEQUENCE LISTING

<160> NUMBER OF SEQ ID NOS: 148

<210> SEQ ID NO 1
<211> LENGTH: 459
<212> TYPE: DNA
<213> ORGANISM: Homo sapiens

<400> SEQUENCE: 1
caagttcctt tatgtgctgt ctcatcattt tggcaagaat tcgccaccat gaaacatctg    60
tggttcttcc ttctcctggt ggcagcggcc cagccggcca tggcccagat gcagctggtg   120
cagtctgggg gaggcttggt acagcctggc aggtccctga ctctcctg tgcagcctct    180 ggattcacct ttgatgatta tgccatgcac tgggtccggc aagctccagg gaagggcctg   240
gagtgggtct caggtattag ttggaatagt ggtagcatag ctatgcgga ctctgtgaag    300 ggccgattca ccatctccag agacaacgcc aagaactccc tgtatctgca aatgaacagt   360
ctgagagctg aggacacggc cttgtattac tgtgcaaaaa cgtcctacgg ggggcttt     420 gatatctggg gccaagggac aatggtcacc gtctcctca                          459

<210> SEQ ID NO 2
<211> LENGTH: 330
<212> TYPE: DNA
<213> ORGANISM: Homo sapiens

<400> SEQUENCE: 2

```
cagcctgtgc tgactcaatc gccctcagcg tctgggaccc ccgggcagag ggtcaccatc      60
tcttgttctg gaaacacttc caacatcgga agttattatg catactggta tcagcaactc     120
ccaggaacgg cccccaaact cctcatctat gataataatc agcggccctc ggggatccct     180
gcccgattct ctggctccaa gtctggcacc tcagcctccc tggccatcag tgggctccag     240
tctgaggatg aggcagatta ttactgtgca acatgggatg acagcctgaa tggtccggtg     300
ttcggcggag ggaccaaggt caccgtccta                                       330
```

<210> SEQ ID NO 3
<211> LENGTH: 118
<212> TYPE: PRT
<213> ORGANISM: Homo sapiens

<400> SEQUENCE: 3

Gln Met Gln Leu Val Gln Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Thr Ser Tyr Gly Gly Ala Phe Asp Ile Trp Gly Gln Gly Thr
            100                 105                 110

Met Val Thr Val Ser Ser
        115

<210> SEQ ID NO 4
<211> LENGTH: 110
<212> TYPE: PRT
<213> ORGANISM: Homo sapiens

<400> SEQUENCE: 4

Gln Pro Val Leu Thr Gln Ser Pro Ser Ala Ser Gly Thr Pro Gly Gln
1               5                   10                  15

Arg Val Thr Ile Ser Cys Ser Gly Asn Thr Ser Asn Ile Gly Ser Tyr
            20                  25                  30

Tyr Ala Tyr Trp Tyr Gln Gln Leu Pro Gly Thr Ala Pro Lys Leu Leu
        35                  40                  45

Ile Tyr Asp Asn Asn Gln Arg Pro Ser Gly Ile Pro Ala Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Pro Val Phe Gly Gly Gly Thr Lys Val Thr Val Leu
            100                 105                 110

<210> SEQ ID NO 5
<211> LENGTH: 351
<212> TYPE: DNA
<213> ORGANISM: Homo sapiens

<400> SEQUENCE: 5

```
caggtgcagc tggtggagtc tggggctgag gtgaagaagc ctggggcctc agtgaaggtc    60
tcctgcaagg cttctggata caccttcacc ggctactata tacattgggt gcgacaggcc   120
cctggacaag gcttgagtg gatgggacgg atcaaccctaacagtggtgg cacaaactat   180
gcacagaagt ttcagggcag ggtcaccatg accagggaca cgtccatcag acggcctac   240
atggaactga gtacactgac atctgacgac acggccgttt attactgtgc gagagaagga   300
aggggcggca tggacgtctg ggccaaggg accacggtca ccgtctcctc a            351
```

<210> SEQ ID NO 6
<211> LENGTH: 336
<212> TYPE: DNA
<213> ORGANISM: Homo sapiens

<400> SEQUENCE: 6

```
gatgttgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttgggatt tattactgca tgcaaggtct acaacctccc   300
atcaccttcg gccaggggac acgactggag attaaa                             336
```

<210> SEQ ID NO 7
<211> LENGTH: 117
<212> TYPE: PRT
<213> ORGANISM: Homo sapiens

<400> SEQUENCE: 7

```
Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Arg Thr Ala Tyr
65                  70                  75                  80

Met Glu Leu Ser Thr Leu Thr Ser Asp Asp Thr Ala Val Tyr Tyr Cys
                85                  90                  95

Ala Arg Glu Gly Arg Gly Gly Met Asp Val Trp Gly Gln Gly Thr Thr
            100                 105                 110

Val Thr Val Ser Ser
        115
```

<210> SEQ ID NO 8
<211> LENGTH: 112
<212> TYPE: PRT
<213> ORGANISM: Homo sapiens

<400> SEQUENCE: 8

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

```
                    20                  25                  30

Asn Gly Tyr Asn Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Leu Gln Pro Pro Ile Thr Phe Gly Gln Gly Thr Arg Leu Glu Ile Lys
                100                 105                 110

<210> SEQ ID NO 9
<211> LENGTH: 342
<212> TYPE: DNA
<213> ORGANISM: Homo sapiens

<400> SEQUENCE: 9
gaggtgcagc tgttggagac cgggggaggc gtggtccagc ctggagggtc cctgagactc      60
tcctgtgcag cctctggatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gagtggtgct     300
tttgatatct ggggccaagg gacaatggtc accgtctctt ca                        342

<210> SEQ ID NO 10
<211> LENGTH: 336
<212> TYPE: DNA
<213> ORGANISM: Homo sapiens

<400> SEQUENCE: 10
gatgttgtga tgactcagtc tccactctcc ctgcccgtca cccttggaca gccggcctcc      60
atctcctgca ggtctagtca gagcctcgta tacagtgatg gaaacaccta cttgagttgg     120
tttcaccaga ggccaggcca atctccaagg cgcctaattt ataaggtttc taatcgggac     180
tttggggtcc cagacagatt cagcggcagt gggtcaggca ctgacttcac actgaagatc     240
agcagggtgg aggctgagga tgttggagtt tattactgca tgcaaggtac acactggcct     300
gggacgttcg gccaggggac caaactggat atcaaa                               336

<210> SEQ ID NO 11
<211> LENGTH: 114
<212> TYPE: PRT
<213> ORGANISM: Homo sapiens

<400> SEQUENCE: 11

Glu Val Gln Leu Leu Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Ser Gly Ala Phe Asp Ile Trp Gly Gln Gly Thr Met Val Thr Val
            100                 105                 110

Ser Ser

<210> SEQ ID NO 12
<211> LENGTH: 112
<212> TYPE: PRT
<213> ORGANISM: Homo sapiens

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser His Ser Leu Val Tyr Ser
            20                  25                  30

Asp Gly Asn Thr Tyr Leu Ser Trp Phe His Gln Arg Pro Gly Gln Ser
        35                  40                  45

Pro Arg Arg Leu Ile Tyr Lys Val Ser Asn Arg Asp Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Gly Thr Phe Gly Gln Gly Thr Lys Leu Asp Ile Lys
            100                 105                 110

<210> SEQ ID NO 13
<211> LENGTH: 369
<212> TYPE: DNA
<213> ORGANISM: Homo sapiens

<400> SEQUENCE: 13
caggtacagc tgcagcagtc aggtccagga ctggtgaagc cctcgcagac cctctcactc     60
tcctgtgcca tctccgggga cagtgtctcc agcaacagtg ttgcttggaa ctggatcagg    120
cagtccccat cgagaggcct tgagtggctg gaaggacat actacaggtc caagtggtat    180
aatgattatg cagtctctgt gaaaagtcga ataaccatca acccagacac atccaagaac    240
cagttctccc tgcagctgag ctctgtgact cccgaggaca cggctgtata ttactgtgca    300
agagccgatg gttcgcgagg gggagggtat gaccagtggg gccagggaac cctggtcacc    360
gtctcttca                                                          369

<210> SEQ ID NO 14
<211> LENGTH: 339
<212> TYPE: DNA
<213> ORGANISM: Homo sapiens

<400> SEQUENCE: 14
gacatcgtga tgacccagtc tccagactcc ctggctgtgt ctctgggcga gagggccacc     60
atcaaatgca gtccagtca gtctatttta tacaggtcca acaataagaa ctacttagct    120
tggtaccaac acaaaccagg acagcctcct aagctgctca tttcctgggc atctacccgg    180
gaatccgggg tccctgaccg attcagtggc agcgggtctg ggacagattt cactctcacc    240
atcaacagcc tgcaggctga agatgtggcg gtttattact gtcagcaata ttatactact    300
cctcagactt ttggccaggg gaccaaggtg gagatcaaa                          339

<210> SEQ ID NO 15
<211> LENGTH: 123
<212> TYPE: PRT
<213> ORGANISM: Homo sapiens

<400> SEQUENCE: 15

Gln Val Gln Leu Gln Gln Ser Gly Pro Gly Leu Val Lys Pro Ser Gln
1               5                   10                  15

Thr Leu Ser Leu Ser Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Ser Ser Val Thr Pro Glu Asp Thr Ala Val
                85                  90                  95

Tyr Tyr Cys Ala Arg Ala Asp Gly Ser Arg Gly Gly Tyr Asp Gln
            100                 105                 110

Trp Gly Gln Gly Thr Leu Val Thr Val Ser Ser
    115                 120

<210> SEQ ID NO 16
<211> LENGTH: 113
<212> TYPE: PRT
<213> ORGANISM: Homo sapiens

<400> SEQUENCE: 16

Asp Ile Val Met Thr Gln Ser Pro Asp Ser Leu Ala Val Ser Leu Gly
1               5                   10                  15

Glu Arg Ala Thr Ile Lys Cys Lys Ser Ser Gln Ser Ile Leu Tyr Arg
            20                  25                  30

Ser Asn Asn Lys Asn Tyr Leu Ala Trp Tyr Gln His Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Thr Thr Pro Gln Thr Phe Gly Gln Gly Thr Lys Val Glu Ile
            100                 105                 110

Lys

<210> SEQ ID NO 17
<211> LENGTH: 348
<212> TYPE: DNA
<213> ORGANISM: Homo sapiens

<400> SEQUENCE: 17
caggtccagt tggtggagtc tgggggaggc gtggtccagc ctggggaggtc cctgagactc      60 tcctgtgcag cctctggatt caccttcagt agctatgcta tgcactgggt ccgccaggct     120
ccaggcaagg ggctggagca ggtggcagtt atatcatatg atggaagtaa taaatactac     180
gtagactccg tgaagggccg attcaccatc tccagagaca attccaagaa cacgctgtat     240

```
ctgcaaatga acagcctgag agctgaggac acggctgtgt attactgtgc gagatctaca      300
tacggtatgg acgtctgggg ccaagggacc acggtcaccg tctcctca                  348
```

<210> SEQ ID NO 18
<211> LENGTH: 333
<212> TYPE: DNA
<213> ORGANISM: Homo sapiens

<400> SEQUENCE: 18

```
gatgttgtga tgactcagtc tccactctcc ctgcccgtca cccttggaca gtcggcctcc       60
atctcctgca ggtctagtca aagcctcgta cacagtgatg aaacaccta cttgaattgg      120 tttcagcaga ggccaggcca atctccaagg cgcctaattt ataaggtttc taatcgggac     180
tccggggtcc cagacagatt cagcggcagt gggtcagaca ctgatttcac actgaaaatc     240
agcagggtgg aggccgagga tgttgggatt tattactgca tgcaaggtac acactggtgg     300
acgttcggcc aagggaccaa gctggatatc aaa                                  333
```

<210> SEQ ID NO 19
<211> LENGTH: 116
<212> TYPE: PRT
<213> ORGANISM: Homo sapiens

<400> SEQUENCE: 19

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Gln Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Thr Tyr Gly Met Asp Val Trp Gly Gln Gly Thr Thr Val
            100                 105                 110

Thr Val Ser Ser
        115
```

<210> SEQ ID NO 20
<211> LENGTH: 111
<212> TYPE: PRT
<213> ORGANISM: Homo sapiens

<400> SEQUENCE: 20

```
Asp Val Val Met Thr Gln Ser Pro Leu Ser Leu Pro Val Thr Leu Gly
1               5                   10                  15

Gln Ser Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Asp Thr Asp Phe Thr Leu Glu Ile
65                  70                  75                  80
```

Ser Arg Val Glu Ala Glu Asp Val Gly Ile Tyr Tyr Cys Met Gln Gly
            85                  90                  95

Thr His Trp Trp Thr Phe Gly Gln Gly Thr Lys Leu Asp Ile Lys
        100                 105                 110

<210> SEQ ID NO 21
<211> LENGTH: 360
<212> TYPE: DNA
<213> ORGANISM: Homo sapiens

<400> SEQUENCE: 21
caggtacagc tgcagcagtc aggtccagga ctggtgaagc cctcgcagac cctctcactc      60
acctgtggca tctccgggga cagtgtctct agcaagagtg ctgcttggaa ctggatcagg     120 cagtccccctt cgagaggcct tgagtggctg gaaggacat actacaggtc caagtggcat     180
aatgattatg cagtatctgt gaaaagtcga ataaccatca acccagacac atccaagaac     240
cagttttccc tgcagctgaa ctctgtgacc cccgaagaca cggctgtgta ttattgtgcg     300
cgcggccaga tgggagcttt ggacgtctgg ggccaaggga ccacggtcac cgtctcctca     360

<210> SEQ ID NO 22
<211> LENGTH: 330
<212> TYPE: DNA
<213> ORGANISM: Homo sapiens

<400> SEQUENCE: 22
cagtctgtgt tgacgcagcc gccctcagcg tctgggaccc ccgggcagag ggtcaccatc      60
tcttgttctg gaagcagctc caacatcgga agttattatg tatactggta ccagcaattc     120
ccaggaacgg cccccaaact cctcatctat ggtaataatc agcggccctc agggtccct      180 gaccgattct ctggctccaa gtctggcacc tcagcctccc tggccatcac tgggctccag     240
gctgaggatg aggctgatta ttactgtcag tcctatgaca gcagcctgag tggtgtgata     300
ttcggcggag ggaccaagct gaccgtccta                                       330

<210> SEQ ID NO 23
<211> LENGTH: 120
<212> TYPE: PRT
<213> ORGANISM: Homo sapiens

<400> SEQUENCE: 23

Gln Val Gln Leu Gln Gln Ser Gly Pro Gly Leu Val Lys Pro Ser Gln
1               5                   10                  15

Thr Leu Ser Leu Thr Cys Gly Ile Ser Gly Asp Ser Val Ser Ser Lys
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp His Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Gln Met Gly Ala Leu Asp Val Trp Gly Gln
            100                 105                 110

Gly Thr Thr Val Thr Val Ser Ser
        115                 120

<210> SEQ ID NO 24
<211> LENGTH: 110
<212> TYPE: PRT
<213> ORGANISM: Homo sapiens

<400> SEQUENCE: 24

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Tyr
            20                  25                  30

Tyr Val Tyr Trp Tyr Gln Gln Phe Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Val Ile Phe Gly Gly Gly Thr Lys Leu Thr Val Leu
            100                 105                 110

<210> SEQ ID NO 25
<211> LENGTH: 357
<212> TYPE: DNA
<213> ORGANISM: Homo sapiens

<400> SEQUENCE: 25
gaggtgcagc tggtgcagtc tggggaggc gtggtccagc ctggagggtc cctgagactc    60
tcctgtgcag cctctggatt caccttcagt agctatgcta tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gaggttggtg    300
gctggtcgaa gtgcttttga tatctggggc caagggacca cggtcaccgt ctcctca       357

<210> SEQ ID NO 26
<211> LENGTH: 324
<212> TYPE: DNA
<213> ORGANISM: Homo sapiens

<400> SEQUENCE: 26
gaaattgtgc tgactcagtc tccagccacc ctgtctgtgt ctccagggga aagagccacc    60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctccgat caccttcggc    300
caagggacac gactggagat taaa                                           324

<210> SEQ ID NO 27
<211> LENGTH: 119
<212> TYPE: PRT
<213> ORGANISM: Homo sapiens

<400> SEQUENCE: 27

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Val Ala Gly Arg Ser Ala Phe Asp Ile Trp Gly Gln Gly
            100                 105                 110

Thr Thr Val Thr Val Ser Ser
        115

<210> SEQ ID NO 28
<211> LENGTH: 108
<212> TYPE: PRT
<213> ORGANISM: Homo sapiens

<400> SEQUENCE: 28

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ile Thr Phe Gly Gln Gly Thr Arg Leu Glu Ile Lys
            100                 105

<210> SEQ ID NO 29
<211> LENGTH: 360
<212> TYPE: DNA
<213> ORGANISM: Homo sapiens

<400> SEQUENCE: 29
caggtacagc tgcagcagtc aggtccagga ctggtgaagc cctcgcagac cctctcactc      60
acctgtggca tctccgggga cagtgtctct agcaagagtg ttacttggaa ctggatcagg     120
gagtctccaa cgggaggcct tgagtggctg ggcaggacat actataggtc caagtggttt     180
aatgattatg cagtatctgt gaaaagtcga ataactgtca acccagacac atccaagaac     240
cagttttccc tgcagctaaa ctctgtgact cccgaggaca ggggtgtcta ttactgcgca     300
cgcgccaaga tgggaggtat ggacgtctgg ggccagggga ccacggtcac cgtctcttca     360

<210> SEQ ID NO 30
<211> LENGTH: 120
<212> TYPE: PRT
<213> ORGANISM: Homo sapiens

<400> SEQUENCE: 30

```
Gln Val Gln Leu Gln Gln Ser Gly Pro Gly Leu Val Lys Pro Ser Gln
1               5                   10                  15

Thr Leu Ser Leu Thr Cys Gly Ile Ser Gly Asp Ser Val Ser Ser Lys
            20                  25                  30

Ser Val Thr Trp Asn Trp Ile Arg Glu Ser Pro Thr Gly Gly Leu Glu
        35                  40                  45

Trp Leu Gly Arg Thr Tyr Tyr Arg Ser Lys Trp Phe Asn Asp Tyr Ala
50                  55                  60

Val Ser Val Lys Ser Arg Ile Thr Val Asn Pro Asp Thr Ser Lys Asn
65                  70                  75                  80

Gln Phe Ser Leu Gln Leu Asn Ser Val Thr Pro Glu Asp Arg Gly Val
                85                  90                  95

Tyr Tyr Cys Ala Arg Ala Lys Met Gly Gly Met Asp Val Trp Gly Gln
            100                 105                 110

Gly Thr Thr Val Thr Val Ser Ser
            115                 120
```

<210> SEQ ID NO 31
<211> LENGTH: 360
<212> TYPE: DNA
<213> ORGANISM: Homo sapiens

<400> SEQUENCE: 31

```
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca acccagacac atccaagaac     240
cagttctccc tgcagctgaa ctctgtgact cccgaggaca cggctgttta ttactgtaca     300
agacagagtt ggcacggtat ggaagtctgg ggccaaggga ccacggtcac cgtctcctca     360
```

<210> SEQ ID NO 32
<211> LENGTH: 120
<212> TYPE: PRT
<213> ORGANISM: Homo sapiens

<400> SEQUENCE: 32

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Thr Arg Gln Ser Trp His Gly Met Glu Val Trp Gly Gln
            100                 105                 110

Gly Thr Thr Val Thr Val Ser Ser
            115                 120
```

<210> SEQ ID NO 33
<211> LENGTH: 360

<212> TYPE: DNA
<213> ORGANISM: Homo sapiens

<400> SEQUENCE: 33

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg ggaaggacat actacaggtc caagtggtat   180
aatgattatg cagtatctgt gaaaagtcga ataaccatca actcagacac atcgaagaac   240
cagttctccc tgcagctgaa gtctgtgact cccgaggaca cggctgtgta ttactgtgca   300
aggagtatag caacaggtac tgactactgg ggccagggaa ccctggtcac cgtctcctca   360
```

<210> SEQ ID NO 34
<211> LENGTH: 120
<212> TYPE: PRT
<213> ORGANISM: Homo sapiens

<400> SEQUENCE: 34

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Ser Asp Thr Ser Lys Asn
65                  70                  75                  80

Gln Phe Ser Leu Gln Leu Lys Ser Val Thr Pro Glu Asp Thr Ala Val
                85                  90                  95

Tyr Tyr Cys Ala Arg Ser Ile Ala Thr Gly Thr Asp Tyr Trp Gly Gln
            100                 105                 110

Gly Thr Leu Val Thr Val Ser Ser
        115                 120
```

<210> SEQ ID NO 35
<211> LENGTH: 360
<212> TYPE: DNA
<213> ORGANISM: Homo sapiens

<400> SEQUENCE: 35

```
caggtacagc tgcagcagtc aggtccagga ctgatgaagc cctcgcagac cctctcactc    60
acctgtgcca tctccgggga cagtgtctct agtagccgtg ctacttggaa ctggatcagg   120
gagtctccaa cggagaggcct tgagtggctg ggcaggacat actataggtc caagtggttt   180
aatgattatg cagtatctgt gaaaagtcga ataactgtca acccagacac atccaagaac   240
cagttttccc tgcagctaaa ctctgtgact cccgaggaca gggtgtcta ttactgcgca   300
cgcgccaaga tgggaggtat ggacgtctgg ggccagggga ccacggtcac cgtctcctca   360
```

<210> SEQ ID NO 36
<211> LENGTH: 120
<212> TYPE: PRT
<213> ORGANISM: Homo sapiens

<400> SEQUENCE: 36

```
Gln Val Gln Leu Gln Gln Ser Gly Pro Gly Leu Met Lys Pro Ser Gln
1               5                   10                  15
```

Thr Leu Ser Leu Thr Cys Ala Ile Ser Gly Asp Ser Val Ser Ser
                20                  25                  30

Arg Ala Thr Trp Asn Trp Ile Arg Glu Ser Pro Thr Gly Leu Glu
            35                  40                  45

Trp Leu Gly Arg Thr Tyr Tyr Arg Ser Lys Trp Phe Asn Asp Tyr Ala
    50                  55                  60

Val Ser Val Lys Ser Arg Ile Thr Val Asn Pro Asp Thr Ser Lys Asn
65                  70                  75                  80

Gln Phe Ser Leu Gln Leu Asn Ser Val Thr Pro Glu Asp Arg Gly Val
                85                  90                  95

Tyr Tyr Cys Ala Arg Ala Lys Met Gly Gly Met Asp Val Trp Gly Gln
            100                 105                 110

Gly Thr Thr Val Thr Val Ser Ser
        115                 120

<210> SEQ ID NO 37
<211> LENGTH: 360
<212> TYPE: DNA
<213> ORGANISM: Homo sapiens

<400> SEQUENCE: 37
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg ggaaggacat actacaggtc caagtggtat     180
aatgattatg cagtatctgt gaaaagtcga ataaccatca acccagacac atccaagaac     240
cagttctccc tgcagctgaa ctctgtgact cccgaggaca cggctgtgta ttactgtgca     300
agaggaacac gttggggtat ggacgtctgg ggccaaggga ccctggtcac tgtctcctca     360

<210> SEQ ID NO 38
<211> LENGTH: 120
<212> TYPE: PRT
<213> ORGANISM: Homo sapiens

<400> SEQUENCE: 38

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Thr Arg Trp Gly Met Asp Val Trp Gly Gln
            100                 105                 110

Gly Thr Leu Val Thr Val Ser Ser
        115                 120

<210> SEQ ID NO 39
<211> LENGTH: 360
<212> TYPE: DNA
<213> ORGANISM: Homo sapiens

<400> SEQUENCE: 39

```
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct gagtggctg ggaaggacat actacaggtc caagtggtat   180
aatgattatg cagtatctgt gaaaagtcga ataaccatca acccagacac atccaagaac   240
cagttctccc tgcagctgaa ctctgtgact cccgaggaca cggctgtgta ttactgtgca   300
agagcgaaag tgtacggtgt ggacgtctgg ggccaaggga ccacggtcac cgtctcctca   360
```

<210> SEQ ID NO 40
<211> LENGTH: 120
<212> TYPE: PRT
<213> ORGANISM: Homo sapiens

<400> SEQUENCE: 40

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Ala Lys Val Tyr Gly Val Asp Val Trp Gly Gln
            100                 105                 110

Gly Thr Thr Val Thr Val Ser Ser
        115                 120
```

<210> SEQ ID NO 41
<211> LENGTH: 360
<212> TYPE: DNA
<213> ORGANISM: Homo sapiens

<400> SEQUENCE: 41

```
caggtacagc tgcagcagtc aggtccagga ctggtgaagc cctcgcagac cctctcactc    60
acctgtggca tctccgggga cagtgtctct agcaagagtg ccacttggaa ctgggtcagg   120
cagtccgcat cgagaggcct gagtggctg ggaaggacat actacaggtc caggtggttt   180
aatgattatg cagtgtctgt gaaaagtcga ataaccgtca agccagacac atccaagaac   240
cagtttcccc tgcaattaaa ttctgtgagt cccgaggaca cggctatcta ttactgtgca   300
cgcggcaaca tgggagctat ggacgtctgg ggccaaggga ccacggtcac cgtctcttca   360
```

<210> SEQ ID NO 42
<211> LENGTH: 120
<212> TYPE: PRT
<213> ORGANISM: Homo sapiens

<400> SEQUENCE: 42

```
Gln Val Gln Leu Gln Gln Ser Gly Pro Gly Leu Val Lys Pro Ser Gln
 1               5                  10                  15

Thr Leu Ser Leu Thr Cys Gly Ile Ser Gly Asp Ser Val Ser Ser Lys
```

```
            20                  25                  30
Ser Ala Thr Trp Asn Trp Val Arg Gln Ser Ala Ser Arg Gly Leu Glu
        35                  40                  45

Trp Leu Gly Arg Thr Tyr Tyr Arg Ser Arg Trp Phe Asn Asp Tyr Ala
 50                  55                  60

Val Ser Val Lys Ser Arg Ile Thr Val Lys Pro Asp Thr Ser Lys Asn
 65                  70                  75                  80

Gln Phe Ser Leu Gln Leu Asn Ser Val Ser Pro Glu Asp Thr Ala Ile
                 85                  90                  95

Tyr Tyr Cys Ala Arg Gly Asn Met Gly Ala Met Asp Val Trp Gly Gln
            100                 105                 110

Gly Thr Thr Val Thr Val Ser Ser
            115                 120
```

<210> SEQ ID NO 43
<211> LENGTH: 357
<212> TYPE: DNA
<213> ORGANISM: Homo sapiens

<400> SEQUENCE: 43

```
caggtacagc tgcagcagtc aggtccagga ctgctgaagc cctcgcagac cctctcactc      60
acctgtgcca tctccgggga cagggtctct agcaatagag ctgcttggaa ctgggtcagg     120
cagtccccat cgagaggcct tgagtggctg ggaaggacat actacaggtc ccagtggtat     180
aatgattatg cagtctctgt aaaaagtcga gtgaccatca gcccagacgc atccaagaac     240
caagtctccc tgcagctgaa ctctgtgact cccgaggaca cggctgtgta ttactgtgca     300
agaggtacag ctatgggtga cgcctggggc cagggaaccc tggtcaccgt ctcttca        357
```

<210> SEQ ID NO 44
<211> LENGTH: 119
<212> TYPE: PRT
<213> ORGANISM: Homo sapiens

<400> SEQUENCE: 44

```
Gln Val Gln Leu Gln Gln Ser Gly Pro Gly Leu Leu Lys Pro Ser Gln
 1               5                  10                  15

Thr Leu Ser Leu Thr Cys Ala Ile Ser Gly Asp Arg Val Ser Ser Asn
            20                  25                  30

Arg Ala Ala Trp Asn Trp Val Arg Gln Ser Pro Ser Arg Gly Leu Glu
        35                  40                  45

Trp Leu Gly Arg Thr Tyr Tyr Arg Ser Gln Trp Tyr Asn Asp Tyr Ala
 50                  55                  60

Val Ser Val Lys Ser Arg Val Thr Ile Ser Pro Asp Ala Ser Lys Asn
 65                  70                  75                  80

Gln Val Ser Leu Gln Leu Asn Ser Val Thr Pro Glu Asp Thr Ala Val
                 85                  90                  95

Tyr Tyr Cys Ala Arg Gly Thr Ala Met Gly Asp Ala Trp Gly Gln Gly
            100                 105                 110

Thr Leu Val Thr Val Ser Ser
        115
```

<210> SEQ ID NO 45
<211> LENGTH: 360
<212> TYPE: DNA
<213> ORGANISM: Homo sapiens

<400> SEQUENCE: 45
caggtacagc tgcagcagtc aggtccagga ctggtgaagc cctcgcagac cctcacactc    60
acctgtgtca tctccgggga cagtgtctct agcaacagtg ctgcttggaa ctggatcagg   120
cagtccccat cgagaggcct tgagtggctg gaaggacat actacaggtc caagtggtat   180
aatgattatg cagtttctct gaaaagtcga ataaccatca acccagacac atccaagaac   240
cagttctccc tgcagctgaa ctctgtgact cccgaggaca cggctgtgta ttactgtgca   300
agacaagcct ccaacggttt tgatatctgg ggccaaggga caatggtcac cgtctcttca   360

<210> SEQ ID NO 46
<211> LENGTH: 120
<212> TYPE: PRT
<213> ORGANISM: Homo sapiens

<400> SEQUENCE: 46

Gln Val Gln Leu Gln Gln Ser Gly Pro Gly Leu Val Lys Pro Ser Gln
1               5                   10                  15

Thr Leu Thr Leu Thr Cys Val Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Leu Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gln Ala Ser Asn Gly Phe Asp Ile Trp Gly Gln
            100                 105                 110

Gly Thr Met Val Thr Val Ser Ser
        115                 120

<210> SEQ ID NO 47
<211> LENGTH: 360
<212> TYPE: DNA
<213> ORGANISM: Homo sapiens

<400> SEQUENCE: 47
caggtacagc tgcagcagtc aggtccagga ctggtgaagc cctcgcagac cctctcactc    60
acctgtgcca tctccgggga cagtgtctct agcaacagtg ctgcttggaa ctggatcagg   120
cagtccccat cgagaggcct tgagtggctg gaaggacat actacaggtc caagtggtat   180
aatgattatg cagtatctgt gaaaagtcga ataaccatca acccagacac atccaagaac   240
cagttctccc tgcagctgaa ctctgtgact cccgaggaca cggctgtgta ttactgtgca   300
agacagggga cgacaggctt tgactactgg ggccagggaa ccacggtcac cgtctcctca   360

<210> SEQ ID NO 48
<211> LENGTH: 120
<212> TYPE: PRT
<213> ORGANISM: Homo sapiens

<400> SEQUENCE: 48

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Gln Gly Thr Gly Phe Asp Tyr Trp Gly Gln
             100                 105                 110

Gly Thr Thr Val Thr Val Ser Ser
            115                 120

<210> SEQ ID NO 49
<211> LENGTH: 330
<212> TYPE: DNA
<213> ORGANISM: Homo sapiens

<400> SEQUENCE: 49
cagtctgtcg tgacgcagcc gccctcagtg tctgcggccc caggacagaa ggtcaccatc      60
tcctgctctg gaagcagctc caacattggg aattattatg tgtcctggta ccagcacctc     120
ccaggaacag cccccaaact cctcatttat gacaatgcta agcgaccctc aggattcct      180 gaccgattct ctggctccaa gtctggcacg tcagccaccc tgggcatcac tgggctccgg     240
gctgaggatg aggctgatta ttactgccag tcctatgaca atagccttag tggtttggtg     300
ttcggcggag ggaccaagct gaccgtccta                                       330

<210> SEQ ID NO 50
<211> LENGTH: 110
<212> TYPE: PRT
<213> ORGANISM: Homo sapiens

<400> SEQUENCE: 50

Gln Ser Val Val Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Tyr
             20                  25                  30

Tyr Val Ser Trp Tyr Gln His Leu Pro Gly Thr Ala Pro Lys Leu Leu
         35                  40                  45

Ile Tyr Asp Asn Ala Lys Arg Pro Ser Gly Ile Pro Asp Arg Phe Ser
 50                  55                  60

Gly Ser Lys Ser Gly Thr Ser Ala Thr Leu Gly Ile Thr Gly Leu Arg
 65                  70                  75                  80

Ala Glu Asp Glu Ala Asp Tyr Tyr Cys Gln Ser Tyr Asp Asn Ser Leu
                 85                  90                  95

Ser Gly Leu Val Phe Gly Gly Gly Thr Lys Leu Thr Val Leu
            100                 105                 110

<210> SEQ ID NO 51
<211> LENGTH: 330
<212> TYPE: DNA
<213> ORGANISM: Homo sapiens

<400> SEQUENCE: 51
cagtctgtgt tgacgcagcc accctcagcg tctgggaccc ccgggcagag ggtcaccatc      60
tcttgttctg gaaccagctc caacatcgga agtaagtatg tatactggta ccagcggctc     120

```
ccaggaacgg cccccaaact cctcatctat actaatgatc agcggccctc agggtccct    180 gcccgattct ctggctccaa gtctggcacc tcagcctccc tggccatcac tgggctccag    240
gctgaggatg aggctgatta ttactgccag tcctatgaca gcagcctgcg tgctgtggtt    300
ttcggcggag ggaccaagct gaccgtccta                                     330
```

<210> SEQ ID NO 52
<211> LENGTH: 110
<212> TYPE: PRT
<213> ORGANISM: Homo sapiens

<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ser Lys
            20                  25                  30

Tyr Val Tyr Trp Tyr Gln Arg Leu Pro Gly Thr Ala Pro Lys Leu Leu
        35                  40                  45

Ile Tyr Thr Asn Asp Gln Arg Pro Ser Gly Val Pro Ala Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Arg Ala Val Val Phe Gly Gly Gly Thr Lys Leu Thr Val Leu
            100                 105                 110

<210> SEQ ID NO 53
<211> LENGTH: 330
<212> TYPE: DNA
<213> ORGANISM: Homo sapiens

<400> SEQUENCE: 53

```
cagtctgtgt tgacgcagcc accctcagcg tctgggaccc ccgggcagag ggtcaccatc     60
tcttgttctg gaaccagctc caacatcgga agtttctatg tatactggta ccagcggctc    120
ccaggaacgg cccccaaact cctcatctat actaatgatc agcggccctc agggtccct    180 gcccgattct ctggctccaa gtctggcacc tcagcctccc tggccatcac tgggctccag    240
gctgaggatg aggctgatta ttactgccag tcctatgaca gcagcctgcg tgctgtggtt    300
ttcggcggag ggaccaagct gaccgtccta                                     330
```

<210> SEQ ID NO 54
<211> LENGTH: 110
<212> TYPE: PRT
<213> ORGANISM: Homo sapiens

<400> SEQUENCE: 54

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ser Phe
            20                  25                  30

Tyr Val Tyr Trp Tyr Gln Arg Leu Pro Gly Thr Ala Pro Lys Leu Leu
        35                  40                  45

Ile Tyr Thr Asn Asp Gln Arg Pro Ser Gly Val Pro Ala Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Arg Ala Val Val Phe Gly Gly Gly Thr Lys Leu Thr Val Leu
            100                 105                 110

<210> SEQ ID NO 55
<211> LENGTH: 330
<212> TYPE: DNA
<213> ORGANISM: Homo sapiens

<400> SEQUENCE: 55
cagtctgtgt tgacgcagcc accctcagcg tctgggaccc ccgggcagag ggtcaccatc      60
tcttgttctg gaaccagctc aacatcgga agtttctatg tatactggta ccagcagctc     120
ccaggaacgg cccccaaact cctcatctat actaatgatc agcggccctc aggggtccct     180
gcccgattct ctggctccaa gtctggcacc tcagcctccc tggccatcac tgggctccag     240
gctgaggatg aggctgatta ttactgccag tcctatgaca gcagcctgcg tgctgtggtt     300
ttcggcggag ggaccaagct gaccgtccta                                     330

<210> SEQ ID NO 56
<211> LENGTH: 110
<212> TYPE: PRT
<213> ORGANISM: Homo sapiens

<400> SEQUENCE: 56

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ser Phe
            20                  25                  30

Tyr Val Tyr Trp Tyr Gln Gln Leu Pro Gly Thr Ala Pro Lys Leu Leu
        35                  40                  45

Ile Tyr Thr Asn Asp Gln Arg Pro Ser Gly Val Pro Ala Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Arg Ala Val Val Phe Gly Gly Gly Thr Lys Leu Thr Val Leu
            100                 105                 110

<210> SEQ ID NO 57
<211> LENGTH: 330
<212> TYPE: DNA
<213> ORGANISM: Homo sapiens

<400> SEQUENCE: 57
cagtctgtgt tgacgcagcc accctcagcg tctgggaccc ccgggcagag ggtcaccatc      60
tcttgttctg gaaccagctc aacatcgga agttactatg tatactggta ccagcagctc     120
ccaggaacgg cccccaaact cctcatctat actaatgatc agcggccctc aggggtccct     180
gcccgattct ctggctccaa gtctggcacc tcagcctccc tggccatcac tgggctccag     240
gctgaggatg aggctgatta ttactgccag tcctatgaca gcagcctgcg tgctgtggtt     300
ttcggcggag ggaccaagct gaccgtccta                                     330

<210> SEQ ID NO 58
<211> LENGTH: 110

```
<212> TYPE: PRT
<213> ORGANISM: Homo sapiens

<400> SEQUENCE: 58

Gln Ser Val Leu Thr Gln Pro Pro Ser Ala Ser Gly Thr Pro Gly Gln
1               5                   10                  15

Arg Val Thr Ile Ser Cys Ser Gly Thr Ser Ser Asn Ile Gly Ser Tyr
            20                  25                  30

Tyr Val Tyr Trp Tyr Gln Gln Leu Pro Gly Thr Ala Pro Lys Leu Leu
        35                  40                  45

Ile Tyr Thr Asn Asp Gln Arg Pro Ser Gly Val Pro Ala Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Arg Ala Val Val Phe Gly Gly Gly Thr Lys Leu Thr Val Leu
            100                 105                 110

<210> SEQ ID NO 59
<211> LENGTH: 10
<212> TYPE: PRT
<213> ORGANISM: Homo sapiens

<400> SEQUENCE: 59

Gly Phe Thr Phe Asp Asp Tyr Ala Met His
1               5                   10

<210> SEQ ID NO 60
<211> LENGTH: 17
<212> TYPE: PRT
<213> ORGANISM: Homo sapiens

<400> SEQUENCE: 60

Gly Ile Ser Trp Asn Ser Gly Ser Ile Gly Tyr Ala Asp Ser Val Lys
1               5                   10                  15

Gly

<210> SEQ ID NO 61
<211> LENGTH: 11
<212> TYPE: PRT
<213> ORGANISM: Homo sapiens

<400> SEQUENCE: 61

Ala Lys Thr Ser Tyr Gly Gly Ala Phe Asp Ile
1               5                   10

<210> SEQ ID NO 62
<211> LENGTH: 13
<212> TYPE: PRT
<213> ORGANISM: Homo sapiens

<400> SEQUENCE: 62

Ser Gly Asn Thr Ser Asn Ile Gly Ser Tyr Tyr Ala Tyr
1               5                   10

<210> SEQ ID NO 63
<211> LENGTH: 7
<212> TYPE: PRT
<213> ORGANISM: Homo sapiens

<400> SEQUENCE: 63
```

```
Asp Asn Asn Gln Arg Pro Ser
1               5

<210> SEQ ID NO 64
<211> LENGTH: 11
<212> TYPE: PRT
<213> ORGANISM: Homo sapiens

<400> SEQUENCE: 64

Ala Thr Trp Asp Asp Ser Leu Asn Gly Pro Val
1               5                   10

<210> SEQ ID NO 65
<211> LENGTH: 9
<212> TYPE: PRT
<213> ORGANISM: Homo sapiens

<400> SEQUENCE: 65

Gly Tyr Thr Thr Gly Tyr Tyr Ile His
1               5

<210> SEQ ID NO 66
<211> LENGTH: 10
<212> TYPE: PRT
<213> ORGANISM: Homo sapiens

<400> SEQUENCE: 66

Arg Ile Asn Pro Asn Ser Gly Gly Thr Asn
1               5                   10

<210> SEQ ID NO 67
<211> LENGTH: 10
<212> TYPE: PRT
<213> ORGANISM: Homo sapiens

<400> SEQUENCE: 67

Ala Arg Glu Gly Arg Gly Gly Met Asp Val
1               5                   10

<210> SEQ ID NO 68
<211> LENGTH: 14
<212> TYPE: PRT
<213> ORGANISM: Homo sapiens

<400> SEQUENCE: 68

Arg Ser Ser Gln Ser Leu Leu His Ser Asn Gly Tyr Asn Tyr
1               5                   10

<210> SEQ ID NO 69
<211> LENGTH: 7
<212> TYPE: PRT
<213> ORGANISM: Homo sapiens

<400> SEQUENCE: 69

Leu Gly Ser Asn Arg Ala Ser
1               5

<210> SEQ ID NO 70
<211> LENGTH: 9
<212> TYPE: PRT
<213> ORGANISM: Homo sapiens

<400> SEQUENCE: 70

Met Gln Gly Leu Gln Pro Pro Ile Thr
```

```
<210> SEQ ID NO 71
<211> LENGTH: 10
<212> TYPE: PRT
<213> ORGANISM: Homo sapiens

<400> SEQUENCE: 71

Gly Phe Thr Phe Ser Ser Tyr Ala Met His
1               5                   10

<210> SEQ ID NO 72
<211> LENGTH: 17
<212> TYPE: PRT
<213> ORGANISM: Homo sapiens

<400> SEQUENCE: 72

Val Ile Ser Tyr Asp Gly Ser Asn Lys Tyr Tyr Ala Asp Ser Val Lys
1               5                   10                  15
Gly

<210> SEQ ID NO 73
<211> LENGTH: 7
<212> TYPE: PRT
<213> ORGANISM: Homo sapiens

<400> SEQUENCE: 73

Ala Ser Gly Ala Phe Asp Ile
1               5

<210> SEQ ID NO 74
<211> LENGTH: 16
<212> TYPE: PRT
<213> ORGANISM: Homo sapiens

<400> SEQUENCE: 74

Arg Ser Ser His Ser Leu Val Tyr Ser Asp Gly Asn Thr Tyr Leu Ser
1               5                   10                  15

<210> SEQ ID NO 75
<211> LENGTH: 7
<212> TYPE: PRT
<213> ORGANISM: Homo sapiens

<400> SEQUENCE: 75

Lys Val Ser Asn Arg Asp Phe
1               5

<210> SEQ ID NO 76
<211> LENGTH: 9
<212> TYPE: PRT
<213> ORGANISM: Homo sapiens

<400> SEQUENCE: 76

Met Gln Gly Thr His Trp Pro Gly Thr
1               5

<210> SEQ ID NO 77
<211> LENGTH: 12
<212> TYPE: PRT
<213> ORGANISM: Homo sapiens

<400> SEQUENCE: 77

Gly Asp Ser Val Ser Ser Asn Ser Val Ala Trp Asn
```

```
<210> SEQ ID NO 78
<211> LENGTH: 18
<212> TYPE: PRT
<213> ORGANISM: Homo sapiens

<400> SEQUENCE: 78

Arg Thr Tyr Tyr Arg Ser Lys Trp Tyr Asn Asp Tyr Ala Val Ser Val
1               5                   10                  15
Lys Ser

<210> SEQ ID NO 79
<211> LENGTH: 13
<212> TYPE: PRT
<213> ORGANISM: Homo sapiens

<400> SEQUENCE: 79

Ala Arg Ala Asp Gly Ser Arg Gly Gly Tyr Asp Gln
1               5                   10

<210> SEQ ID NO 80
<211> LENGTH: 17
<212> TYPE: PRT
<213> ORGANISM: Homo sapiens

<400> SEQUENCE: 80

Lys Ser Ser Gln Ser Ile Leu Tyr Arg Ser Asn Asn Lys Asn Tyr Leu
1               5                   10                  15
Ala

<210> SEQ ID NO 81
<211> LENGTH: 7
<212> TYPE: PRT
<213> ORGANISM: Homo sapiens

<400> SEQUENCE: 81

Trp Ala Ser Thr Arg Glu Ser
1               5

<210> SEQ ID NO 82
<211> LENGTH: 9
<212> TYPE: PRT
<213> ORGANISM: Homo sapiens

<400> SEQUENCE: 82

Gln Gln Tyr Tyr Thr Thr Pro Gln Thr
1               5

<210> SEQ ID NO 83
<211> LENGTH: 10
<212> TYPE: PRT
<213> ORGANISM: Homo sapiens

<400> SEQUENCE: 83

Gly Phe Thr Phe Ser Ser Tyr Ala Met His
1               5                   10

<210> SEQ ID NO 84
<211> LENGTH: 17
<212> TYPE: PRT
<213> ORGANISM: Homo sapiens

<400> SEQUENCE: 84
```

Val Ile Ser Tyr Asp Gly Ser Asn Lys Tyr Tyr Val Asp Ser Val Lys
1               5                   10                  15

Gly

<210> SEQ ID NO 85
<211> LENGTH: 9
<212> TYPE: PRT
<213> ORGANISM: Homo sapiens

<400> SEQUENCE: 85

Ala Arg Ser Thr Tyr Gly Met Asp Val
1               5

<210> SEQ ID NO 86
<211> LENGTH: 16
<212> TYPE: PRT
<213> ORGANISM: Homo sapiens

<400> SEQUENCE: 86

Arg Ser Ser Gln Ser Leu Val His Ser Asp Gly Asn Thr Tyr Leu Asn
1               5                   10                  15

<210> SEQ ID NO 87
<211> LENGTH: 7
<212> TYPE: PRT
<213> ORGANISM: Homo sapiens

<400> SEQUENCE: 87

Lys Val Ser Asn Arg Asp Ser
1               5

<210> SEQ ID NO 88
<211> LENGTH: 8
<212> TYPE: PRT
<213> ORGANISM: Homo sapiens

<400> SEQUENCE: 88

Met Gln Gly Thr His Trp Trp Thr
1               5

<210> SEQ ID NO 89
<211> LENGTH: 12
<212> TYPE: PRT
<213> ORGANISM: Homo sapiens

<400> SEQUENCE: 89

Gly Asp Ser Val Ser Ser Lys Ser Ala Ala Trp Asn
1               5                   10

<210> SEQ ID NO 90
<211> LENGTH: 15
<212> TYPE: PRT
<213> ORGANISM: Homo sapiens

<400> SEQUENCE: 90

Arg Thr Tyr Tyr Arg Ser Lys Trp His Asn Asp Tyr Ala Val Ser
1               5                   10                  15

<210> SEQ ID NO 91
<211> LENGTH: 10
<212> TYPE: PRT
<213> ORGANISM: Homo sapiens

<400> SEQUENCE: 91

Ala Arg Gly Gln Met Gly Ala Leu Asp Val
1               5                   10

<210> SEQ ID NO 92
<211> LENGTH: 15
<212> TYPE: PRT
<213> ORGANISM: Homo sapiens

<400> SEQUENCE: 92

Ser Gly Ser Ser Ser Asn Ile Gly Ser Tyr Tyr Val Tyr Trp Tyr
1               5                   10                  15

<210> SEQ ID NO 93
<211> LENGTH: 7
<212> TYPE: PRT
<213> ORGANISM: Homo sapiens

<400> SEQUENCE: 93

Gly Asn Asn Gln Arg Pro Ser
1               5

<210> SEQ ID NO 94
<211> LENGTH: 11
<212> TYPE: PRT
<213> ORGANISM: Homo sapiens

<400> SEQUENCE: 94

Gln Ser Tyr Asp Ser Ser Leu Ser Gly Val Ile
1               5                   10

<210> SEQ ID NO 95
<211> LENGTH: 10
<212> TYPE: PRT
<213> ORGANISM: Homo sapiens

<400> SEQUENCE: 95

Gly Phe Thr Phe Ser Ser Tyr Ala Met His
1               5                   10

<210> SEQ ID NO 96
<211> LENGTH: 17
<212> TYPE: PRT
<213> ORGANISM: Homo sapiens

<400> SEQUENCE: 96

Val Ile Ser Tyr Asp Gly Ser Asn Lys Tyr Tyr Ala Asp Ser Val Lys
1               5                   10                  15
Gly

<210> SEQ ID NO 97
<211> LENGTH: 12
<212> TYPE: PRT
<213> ORGANISM: Homo sapiens

<400> SEQUENCE: 97

Ala Arg Leu Val Ala Gly Arg Ser Ala Phe Asp Ile
1               5                   10

<210> SEQ ID NO 98
<211> LENGTH: 11
<212> TYPE: PRT
<213> ORGANISM: Homo sapiens

<400> SEQUENCE: 98

Arg Ala Ser Gln Ser Val Ser Ser Asn Leu Ala
1               5                   10

<210> SEQ ID NO 99
<211> LENGTH: 7
<212> TYPE: PRT
<213> ORGANISM: Homo sapiens

<400> SEQUENCE: 99

Gly Ala Ser Thr Arg Ala Thr
1               5

<210> SEQ ID NO 100
<211> LENGTH: 10
<212> TYPE: PRT
<213> ORGANISM: Homo sapiens

<400> SEQUENCE: 100

Gln Gln Tyr Asn Asn Trp Pro Pro Ile Thr
1               5                   10

<210> SEQ ID NO 101
<211> LENGTH: 12
<212> TYPE: PRT
<213> ORGANISM: Homo sapiens

<400> SEQUENCE: 101

Gly Asp Ser Val Ser Ser Lys Ser Val Thr Trp Asn
1               5                   10

<210> SEQ ID NO 102
<211> LENGTH: 15
<212> TYPE: PRT
<213> ORGANISM: Homo sapiens

<400> SEQUENCE: 102

Arg Thr Tyr Tyr Arg Ser Lys Trp Phe Asn Asp Tyr Ala Val Ser
1               5                   10                  15

<210> SEQ ID NO 103
<211> LENGTH: 10
<212> TYPE: PRT
<213> ORGANISM: Homo sapiens

<400> SEQUENCE: 103

Ala Arg Ala Lys Met Gly Gly Met Asp Val
1               5                   10

<210> SEQ ID NO 104
<211> LENGTH: 12
<212> TYPE: PRT
<213> ORGANISM: Homo sapiens

<400> SEQUENCE: 104

Gly Asp Ser Val Ser Ser Asn Ser Ala Ala Trp Asn
1               5                   10

<210> SEQ ID NO 105
<211> LENGTH: 15
<212> TYPE: PRT
<213> ORGANISM: Homo sapiens

<400> SEQUENCE: 105

Arg Thr Tyr Tyr Arg Ser Lys Trp Tyr Asn Asp Tyr Ala Val Ser

<210> SEQ ID NO 106
<211> LENGTH: 10
<212> TYPE: PRT
<213> ORGANISM: Homo sapiens

<400> SEQUENCE: 106

Thr Arg Gln Ser Trp His Gly Met Glu Val
1               5                   10

<210> SEQ ID NO 107
<211> LENGTH: 12
<212> TYPE: PRT
<213> ORGANISM: Homo sapiens

<400> SEQUENCE: 107

Gly Asp Ser Val Ser Ser Asn Ser Ala Ala Trp Asn
1               5                   10

<210> SEQ ID NO 108
<211> LENGTH: 15
<212> TYPE: PRT
<213> ORGANISM: Homo sapiens

<400> SEQUENCE: 108

Arg Thr Tyr Tyr Arg Ser Lys Trp Tyr Asn Asp Tyr Ala Val Ser
1               5                   10                  15

<210> SEQ ID NO 109
<211> LENGTH: 10
<212> TYPE: PRT
<213> ORGANISM: Homo sapiens

<400> SEQUENCE: 109

Ala Arg Ser Ile Ala Thr Gly Thr Asp Tyr
1               5                   10

<210> SEQ ID NO 110
<211> LENGTH: 12
<212> TYPE: PRT
<213> ORGANISM: Homo sapiens

<400> SEQUENCE: 110

Gly Asp Ser Val Ser Ser Ser Arg Ala Thr Trp Asn
1               5                   10

<210> SEQ ID NO 111
<211> LENGTH: 15
<212> TYPE: PRT
<213> ORGANISM: Homo sapiens

<400> SEQUENCE: 111

Arg Thr Tyr Tyr Arg Ser Lys Trp Phe Asn Asp Tyr Ala Val Ser
1               5                   10                  15

<210> SEQ ID NO 112
<211> LENGTH: 10
<212> TYPE: PRT
<213> ORGANISM: Homo sapiens

<400> SEQUENCE: 112

Ala Arg Ala Lys Met Gly Gly Met Asp Val
1               5                   10

<210> SEQ ID NO 113
<211> LENGTH: 12
<212> TYPE: PRT
<213> ORGANISM: Homo sapiens

<400> SEQUENCE: 113

Gly Asp Ser Val Ser Ser Asn Ser Ala Ala Trp Asn
1               5                   10

<210> SEQ ID NO 114
<211> LENGTH: 15
<212> TYPE: PRT
<213> ORGANISM: Homo sapiens

<400> SEQUENCE: 114

Arg Thr Tyr Tyr Arg Ser Lys Trp Tyr Asn Asp Tyr Ala Val Ser
1               5                   10                  15

<210> SEQ ID NO 115
<211> LENGTH: 10
<212> TYPE: PRT
<213> ORGANISM: Homo sapiens

<400> SEQUENCE: 115

Ala Arg Gly Thr Arg Trp Gly Met Asp Val
1               5                   10

<210> SEQ ID NO 116
<211> LENGTH: 12
<212> TYPE: PRT
<213> ORGANISM: Homo sapiens

<400> SEQUENCE: 116

Gly Asp Ser Val Ser Ser Asn Ser Ala Ala Trp Asn
1               5                   10

<210> SEQ ID NO 117
<211> LENGTH: 15
<212> TYPE: PRT
<213> ORGANISM: Homo sapiens

<400> SEQUENCE: 117

Arg Thr Tyr Tyr Arg Ser Lys Trp Tyr Asn Asp Tyr Ala Val Ser
1               5                   10                  15

<210> SEQ ID NO 118
<211> LENGTH: 10
<212> TYPE: PRT
<213> ORGANISM: Homo sapiens

<400> SEQUENCE: 118

Ala Arg Ala Lys Val Tyr Gly Val Asp Val
1               5                   10

<210> SEQ ID NO 119
<211> LENGTH: 12
<212> TYPE: PRT
<213> ORGANISM: Homo sapiens

<400> SEQUENCE: 119

Gly Asp Ser Val Ser Ser Lys Ser Ala Thr Trp Asn
1               5                   10

<210> SEQ ID NO 120

```
<211> LENGTH: 15
<212> TYPE: PRT
<213> ORGANISM: Homo sapiens

<400> SEQUENCE: 120

Arg Thr Tyr Tyr Arg Ser Arg Trp Phe Asn Asp Tyr Ala Val Ser
1               5                   10                  15

<210> SEQ ID NO 121
<211> LENGTH: 10
<212> TYPE: PRT
<213> ORGANISM: Homo sapiens

<400> SEQUENCE: 121

Ala Arg Gly Asn Met Gly Ala Met Asp Val
1               5                   10

<210> SEQ ID NO 122
<211> LENGTH: 12
<212> TYPE: PRT
<213> ORGANISM: Homo sapiens

<400> SEQUENCE: 122

Gly Asp Arg Val Ser Ser Asn Arg Ala Ala Trp Asn
1               5                   10

<210> SEQ ID NO 123
<211> LENGTH: 15
<212> TYPE: PRT
<213> ORGANISM: Homo sapiens

<400> SEQUENCE: 123

Arg Thr Tyr Tyr Arg Ser Gln Trp Tyr Asn Asp Tyr Ala Val Ser
1               5                   10                  15

<210> SEQ ID NO 124
<211> LENGTH: 9
<212> TYPE: PRT
<213> ORGANISM: Homo sapiens

<400> SEQUENCE: 124

Ala Arg Gly Thr Ala Met Gly Asp Ala
1               5

<210> SEQ ID NO 125
<211> LENGTH: 12
<212> TYPE: PRT
<213> ORGANISM: Homo sapiens

<400> SEQUENCE: 125

Gly Asp Ser Val Ser Ser Asn Ser Ala Ala Trp Asn
1               5                   10

<210> SEQ ID NO 126
<211> LENGTH: 15
<212> TYPE: PRT
<213> ORGANISM: Homo sapiens

<400> SEQUENCE: 126

Arg Thr Tyr Tyr Arg Ser Lys Trp Tyr Asn Asp Tyr Ala Val Ser
1               5                   10                  15

<210> SEQ ID NO 127
<211> LENGTH: 10
<212> TYPE: PRT
```

<213> ORGANISM: Homo sapiens

<400> SEQUENCE: 127

Ala Arg Gln Ala Ser Asn Gly Phe Asp Ile
1               5                   10

<210> SEQ ID NO 128
<211> LENGTH: 12
<212> TYPE: PRT
<213> ORGANISM: Homo sapiens

<400> SEQUENCE: 128

Gly Asp Ser Val Ser Ser Asn Ser Ala Ala Trp Asn
1               5                   10

<210> SEQ ID NO 129
<211> LENGTH: 15
<212> TYPE: PRT
<213> ORGANISM: Homo sapiens

<400> SEQUENCE: 129

Arg Thr Tyr Tyr Arg Ser Lys Trp Tyr Asn Asp Tyr Ala Val Ser
1               5                   10                  15

<210> SEQ ID NO 130
<211> LENGTH: 10
<212> TYPE: PRT
<213> ORGANISM: Homo sapiens

<400> SEQUENCE: 130

Ala Arg Gln Gly Thr Thr Gly Phe Asp Tyr
1               5                   10

<210> SEQ ID NO 131
<211> LENGTH: 15
<212> TYPE: PRT
<213> ORGANISM: Homo sapiens

<400> SEQUENCE: 131

Ser Gly Ser Ser Ser Asn Ile Gly Asn Tyr Tyr Val Ser Trp Tyr
1               5                   10                  15

<210> SEQ ID NO 132
<211> LENGTH: 7
<212> TYPE: PRT
<213> ORGANISM: Homo sapiens

<400> SEQUENCE: 132

Asp Asn Ala Lys Arg Pro Ser
1               5

<210> SEQ ID NO 133
<211> LENGTH: 11
<212> TYPE: PRT
<213> ORGANISM: Homo sapiens

<400> SEQUENCE: 133

Gln Ser Tyr Asp Asn Ser Leu Ser Gly Leu Val
1               5                   10

<210> SEQ ID NO 134
<211> LENGTH: 15
<212> TYPE: PRT
<213> ORGANISM: Homo sapiens

<400> SEQUENCE: 134

Ser Gly Thr Ser Ser Asn Ile Gly Ser Lys Tyr Val Tyr Trp Tyr
1               5                   10                  15

<210> SEQ ID NO 135
<211> LENGTH: 7
<212> TYPE: PRT
<213> ORGANISM: Homo sapiens

<400> SEQUENCE: 135

Thr Asn Asp Gln Arg Pro Ser
1               5

<210> SEQ ID NO 136
<211> LENGTH: 11
<212> TYPE: PRT
<213> ORGANISM: Homo sapiens

<400> SEQUENCE: 136

Gln Ser Tyr Asp Ser Ser Leu Arg Ala Val Val
1               5                   10

<210> SEQ ID NO 137
<211> LENGTH: 15
<212> TYPE: PRT
<213> ORGANISM: Homo sapiens

<400> SEQUENCE: 137

Ser Gly Thr Ser Ser Asn Ile Gly Ser Phe Tyr Val Tyr Trp Tyr
1               5                   10                  15

<210> SEQ ID NO 138
<211> LENGTH: 7
<212> TYPE: PRT
<213> ORGANISM: Homo sapiens

<400> SEQUENCE: 138

Thr Asn Asp Gln Arg Pro Ser
1               5

<210> SEQ ID NO 139
<211> LENGTH: 11
<212> TYPE: PRT
<213> ORGANISM: Homo sapiens

<400> SEQUENCE: 139

Gln Ser Tyr Asp Ser Ser Leu Arg Ala Val Val
1               5                   10

<210> SEQ ID NO 140
<211> LENGTH: 15
<212> TYPE: PRT
<213> ORGANISM: Homo sapiens

<400> SEQUENCE: 140

Ser Gly Thr Ser Ser Asn Ile Gly Ser Phe Tyr Val Tyr Trp Tyr
1               5                   10                  15

<210> SEQ ID NO 141
<211> LENGTH: 7
<212> TYPE: PRT
<213> ORGANISM: Homo sapiens

<400> SEQUENCE: 141

Thr Asn Asp Gln Arg Pro Ser
1               5

<210> SEQ ID NO 142
<211> LENGTH: 11
<212> TYPE: PRT
<213> ORGANISM: Homo sapiens

<400> SEQUENCE: 142

Gln Ser Tyr Asp Ser Ser Leu Arg Ala Val Val
1               5                   10

<210> SEQ ID NO 143
<211> LENGTH: 15
<212> TYPE: PRT
<213> ORGANISM: Homo sapiens

<400> SEQUENCE: 143

Ser Gly Thr Ser Ser Asn Ile Gly Ser Tyr Tyr Val Tyr Trp Tyr
1               5                   10                  15

<210> SEQ ID NO 144
<211> LENGTH: 7
<212> TYPE: PRT
<213> ORGANISM: Homo sapiens

<400> SEQUENCE: 144

Thr Asn Asp Gln Arg Pro Ser
1               5

<210> SEQ ID NO 145
<211> LENGTH: 11
<212> TYPE: PRT
<213> ORGANISM: Homo sapiens

<400> SEQUENCE: 145

Gln Ser Tyr Asp Ser Ser Leu Arg Ala Val Val
1               5                   10

<210> SEQ ID NO 146
<211> LENGTH: 47
<212> TYPE: PRT
<213> ORGANISM: Hepatitis B virus

<400> SEQUENCE: 146

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 147
<211> LENGTH: 57
<212> TYPE: PRT
<213> ORGANISM: Hepatitis B virus

<400> SEQUENCE: 147

Gly Gly Trp Ser Ser Lys Pro Arg Gln Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Gly Ala Asn Ser Asn Asn Pro Asp Trp Asp Phe Asn Pro Asn Lys

```
                35                  40                  45

Asp His Trp Pro Glu Ala Asn Gln Val
    50                  55

<210> SEQ ID NO 148
<211> LENGTH: 60
<212> TYPE: PRT
<213> ORGANISM: Homo sapiens

<400> SEQUENCE: 148

Asn Asp Tyr Ala Val Ser Val Lys Ser Arg Ile Thr Ile Asn Pro Asp
1               5                   10                  15

Thr Ser Lys Asn Gln Phe Ser Leu Gln Leu Asn Ser Val Thr Pro Glu
            20                  25                  30

Asp Thr Ala Val Tyr Tyr Cys Ala Arg Gly Lys Met Gly Gly Met Asp
        35                  40                  45

Val Trp Gly Gln Gly Thr Thr Val Thr Val Ser Ser
    50                  55                  60
```

ANTI-PRE-S1 HBV ANTIBODIES

CROSS REFERENCE TO RELATED APPLICATIONS

This application is continuation of U.S. application Ser. No.: 15/566,555, filed Oct. 13, 2017, which is a U.S. National Phase of PCT/CN2016/082985, filed May 23, 2016, which claims priority from PCT/CN2015/079534, filed May 22, 2015, each of which is incorporated herein by reference in their entireties.

INTRODUCTION

More than one third of the world population has been infected by Hepatitis B virus (HBV), and 240 million people are presently chronically infected. HBV infection and related diseases result in about one million deaths annually.

The surface antigen of HBV is composed of Large (L), Middle (M) and Small (S) proteins. The L and M proteins have additional domains at their N terminal as compared to the S protein which only has the S domain. L contains Pre-S1, Pre-S2, and S domains; M contains Pre-S2 and S domains; S protein contains only the S domain. The pre-S1 domain in L protein is the target molecule of HBV receptor(s) expressed on human hepatic cell surface, and antibodies to the pre-S1 domain of HBV have been reported, e.g. Watashi et al, Int. J. Mol. Sci. 2014, 15, 2892-2905, refs 22-27. Relevant literature includes descriptions of the HBV receptor in WO2013159243A1, a humanized antibody from mouse hybridoma, KR127 in U.S. Pat. No. 7,115,723, and pre-S1 peptides in U.S. Pat. No. 7,892,754.

SUMMARY OF THE INVENTION

The invention provides methods and compositions for immune-activation by inhibiting HBV and/or HDV. In one aspect, the invention provides an antibody antigen binding domain which specifically binds HBV Pre-S1, and comprises complementarity determining region (CDR) 1, CDR2 and CDR3, in a combination selected from (a)-(r) as follows, wherein the antibody (Ab), heavy chain (HC) or light chain (LC) and CDR nomenclature system (Kabat, IMGT or composite) from which the CDR combinations derive are shown in the first column, and residues in bold text are Kabat system, and residues underlined are IMGT system:

HCDRs of Unique HBV Pre-S1 Specific Antibodies

| MAbs | CDR1 | CDR2 | CDR3 |
|---|---|---|---|
| m36-HC | GFTFDDYAMH<br>K: SEQ ID NO: 59, res. 6-10<br>I: SEQ ID NO: 59, res. 1-8<br>C: SEQ ID NO: 59 | GISWNSGSIGYADSVKG<br>K: SEQ ID NO: 60<br>I: SEQ ID NO: 60, res. 2-9<br>C: SEQ ID NO: 60 | AKTSYGGAFDI<br>K: SEQ ID NO: 61, res. 3-11<br>I: SEQ ID NO: 61<br>C: SEQ ID NO: 61 |
| m36-LC | SGNTSNIGSYYAY<br>K: SEQ ID NO: 62<br>I: SEQ ID NO: 62, res. 4-11<br>C: SEQ ID NO: 62 | DNNQRPS<br>K: SEQ ID NO: 63<br>I: SEQ ID NO: 63, res. 1-3<br>C: SEQ ID NO: 63 | ATWDDSLNGPV<br>K: SEQ ID NO: 64<br>I: SEQ ID NO: 64<br>C: SEQ ID NO: 64 |
| 71-HC | GYTTGYYIH<br>K: SEQ ID NO: 65, res. 5-9<br>I: SEQ ID NO: 65, res. 1-7<br>C: SEQ ID NO: 65 | RINPNSGGTN<br>K: SEQ ID NO: 66<br>I: SEQ ID NO: 66<br>C: SEQ ID NO: 66 | AREGRGGMDV<br>K: SEQ ID NO: 67, res. 3-10<br>I: SEQ ID NO: 67<br>C: SEQ ID NO: 67 |
| 71-LC | RSSQSLLHSNGYNY<br>K: SEQ ID NO: 68, res. 1-12<br>I: SEQ ID NO: 68, res. 4-14<br>C: SEQ ID NO: 68 | LGSNRAS<br>K: SEQ ID NO: 69<br>I: SEQ ID NO: 69<br>C: SEQ ID NO: 69 | MQGLQPPIT<br>K: SEQ ID NO: 70<br>I: SEQ ID NO: 70<br>C: SEQ ID NO: 70 |
| 76-HC | GFTFSSYAMH<br>K: SEQ ID NO: 71, res. 6-10<br>I: SEQ ID NO: 71, res. 1-8<br>C: SEQ ID NO: 71 | VISYDGSNKYYADSVKG<br>K: SEQ ID NO: 72<br>I: SEQ ID NO: 72, res. 2-9<br>C: SEQ ID NO: 72 | ASGAFDI<br>K: SEQ ID NO: 73, res. 3-7<br>I: SEQ ID NO: 73<br>C: SEQ ID NO: 73 |
| 76-LC | RSSHSLVYSDGNTYLS<br>K: SEQ ID NO: 74<br>I: SEQ ID NO: 74, res. 4-14<br>C: SEQ ID NO: 74 | KVSNRDF<br>K: SEQ ID NO: 75<br>I: SEQ ID NO: 75, res. 1-3<br>C: SEQ ID NO: 75 | MQGTHWPGT<br>K: SEQ ID NO: 76<br>I: SEQ ID NO: 76<br>C: SEQ ID NO: 76 |
| T47-HC | GDSVSSNSVAWN<br>K: SEQ ID NO: 77, res. 6-12<br>I: SEQ ID NO: 77, res. 1-10<br>C: SEQ ID NO: 77 | RTYYRSKWYNDYAVSVKS<br>K: SEQ ID NO: 78<br>I: SEQ ID NO: 78, res. 2-10<br>C: SEQ ID NO: 78 | ARADGSRGGGYDQ<br>K: SEQ ID NO: 79, res. 3-13<br>I: SEQ ID NO: 79<br>C: SEQ ID NO: 79 |
| T47-LC | KSSQSILYRSNNKNYLA<br>K: SEQ ID NO: 80<br>I: SEQ ID NO: 80, res. 4-15<br>C: SEQ ID NO: 80 | WASTRES<br>K: SEQ ID NO: 81<br>I: SEQ ID NO: 81, res. 1-3<br>C: SEQ ID NO: 81 | QQYYTTPQT<br>K: SEQ TD NO: 82<br>I: SEQ ID NO: 82, res. 1-8<br>C: SEQ ID NO: 82 |
| m1Q-HC | GFTFSSYAMH<br>K: SEQ ID NO: 83, res. 6-10<br>I: SEQ ID NO: 83, res. 1-8<br>C: SEQ ID NO: 83 | VISYDGSNKYYVDSVKG<br>K: SEQ ID NO: 84<br>I: SEQ ID NO: 84, res. 2-9<br>C: SEQ ID NO: 84 | ARSTYGMDV<br>K: SEQ ID NO: 85, res. 3-9<br>I: SEQ ID NO: 85<br>C: SEQ ID NO: 85 |

-continued

| MAbs | CDR1 | CDR2 | CDR3 |
|---|---|---|---|
| m1Q-LC | RSSQSLVHSDGNTYLN<br>K: SEQ ID NO: 86<br>I: SEQ ID NO: 86, res. 4-14<br>C: SEQ ID NO: 86 | KVSNRDS<br>K: SEQ ID NO: 87<br>I: SEQ ID NO: 87, res. 1-3<br>C: SEQ ID NO: 87 | MQGTHWWT<br>K: SEQ ID NO: 88<br>I: SEQ ID NO: 88<br>C: SEQ ID NO: 88 |
| 2H5-HC | GDSVSSKSAAWN<br>K: SEQ ID NO: 89, res. 6-12<br>I: SEQ ID NO: 89, res. 1-10<br>C: SEQ ID NO: 89 | RTYYRSKWHNDYAVS<br>K: SEQ ID NO: 90<br>I: SEQ ID NO: 90, res. 3-10<br>C: SEQ ID NO: 90 | ARGQMGALDV<br>K: SEQ ID NO: 91, res. 3-10<br>I: SEQ ID NO: 91<br>C: SEQ ID NO: 91 |
| 2H5-LC | SGSSSNIGSYYVYWY<br>K: SEQ ID NO: 92<br>I: SEQ ID NO: 92, res. 4-11<br>C: SEQ ID NO: 92 | GNNQRPS<br>K: SEQ ID NO: 93<br>I: SEQ ID NO: 93, res. 1-3<br>C: SEQ ID NO: 93 | QSYDSSLSGVI<br>K: SEQ ID NO: 94<br>I: SEQ ID NO: 94<br>C: SEQ ID NO: 94 |
| m150-HC | GFTFSSYAMH<br>K: SEQ ID NO: 95, res. 6-10<br>I: SEQ ID NO: 95, res. 1-8<br>C: SEQ ID NO: 95 | VISYDGSNKYYADSVKG<br>K: SEQ ID NO: 96<br>I: SEQ ID NO: 96, res. 2-9<br>C: SEQ ID NO: 96 | ARLVAGRSAFDI<br>K: SEQ ID NO: 97, res. 3-12<br>I: SEQ ID NO: 97<br>C: SEQ ID NO: 97 |
| m150-LC | RASQSVSSNLA<br>K: SEQ ID NO: 98<br>I: SEQ ID NO: 98, res. 4-9<br>C: SEQ ID NO: 98 | GASTRAT<br>K: SEQ ID NO: 99<br>I: SEQ ID NO: 99, res. 1-3<br>C: SEQ ID NO: 99 | QQYNNWPPIT<br>K: SEQ ID NO: 100<br>I: SEQ ID NO: 100<br>C: SEQ ID NO: 100 |

HCDRs of Antibodies Derived from 2H5
VH-Chain Shuffled Libraries

| MAbs | HCDR1 | HCDR2 | HCDR3 |
|---|---|---|---|
| #4 VH | GDSVSSKSVTWN<br>K: SEQ ID NO: 101, res 6-12<br>I: SEQ ID NO: 101, res. 1-10<br>C: SEQ ID NO: 101 | RTYYRSKWFNDYAVS<br>K: SEQ ID NO: 102<br>I: SEQ ID NO: 102, res. 2-10<br>C: SEQ ID NO: 102 | ARAKMGGMDV<br>K: SEQ ID NO: 103, res 3-10<br>I: SEQ ID NO: 103<br>C: SEQ ID NO: 103 |
| #31 CH | GDSVSSNSAAWN<br>K: SEQ ID NO: 104, res 6-12<br>I: SEQ ID NO: 104, res. 1-10<br>C: SEQ ID NO: 104 | RTYYRSKWYNDYAVS<br>K: SEQ ID NO: 105<br>I: SEQ ID NO: 105, res. 2-10<br>C: SEQ ID NO: 105 | TRQSWHGMEV<br>K: SEQ ID NO: 106, res 3-10<br>I: SEQ ID NO: 106<br>C: SEQ ID NO: 106 |
| #32 VH | GDSVSSNSAAWN<br>K: SEQ ID NO: 107, res 6-12<br>I: SEQ ID NO: 107, res. 1-10<br>C: SEQ ID NO: 107 | RTYYRSKWYNDYAVS<br>K: SEQ ID NO: 108<br>I: SEQ ID NO: 108, res. 2-10<br>C: SEQ ID NO: 108 | ARSIATGTDY<br>K: SEQ ID NO: 109, res 3-10<br>I: SEQ ID NO: 109<br>C: SEQ ID NO: 109 |
| #69 VH | GDSVSSSRATWN<br>K: SEQ ID NO: 110, res 6-12<br>I: SEQ ID NO: 110, res. 1-10<br>C: SEQ ID NO: 110 | RTYYRSKWFNDYAVS<br>K: SEQ ID NO: 111<br>I: SEQ ID NO: 111, res. 2-10<br>C: SEQ ID NO: 111 | ARAKMGGMDV<br>K: SEQ ID NO: 112, res 3-10<br>I: SEQ ID NO: 112<br>C: SEQ ID NO: 112 |
| A14 VH | GDSVSSNSAAWN<br>K: SEQ ID NO: 113, res 6-12<br>I: SEQ ID NO: 113, res. 1-10<br>C: SEQ ID NO: 113 | RTYYRSKWYNDYAVS<br>K: SEQ ID NO: 114<br>I: SEQ ID NO: 114, res. 2-10<br>C: SEQ ID NO: 114 | ARGTRWGMDV<br>K: SEQ ID NO: 115, res 3-10<br>I: SEQ ID NO: 115<br>C: SEQ ID NO: 115 |
| A21 VH | GDSVSSNSAAWN<br>K: SEQ ID NO: 116, res 6-12<br>I: SEQ ID NO: 116, res. 1-10<br>C: SEQ ID NO: 116 | RTYYRSKWYNDYAVS<br>K: SEQ ID NO: 117<br>I: SEQ ID NO: 117, res. 2-10<br>C: SEQ ID NO: 117 | ARAKVYGVDV<br>K: SEQ ID NO: 118, res 3-10<br>I: SEQ ID NO: 118<br>C: SEQ ID NO: 118 |
| B103 VH | GDSVSSKSATWN<br>K: SEQ ID NO: 119, res 6-12<br>I: SEQ ID NO: 119, res. 1-10<br>C: SEQ ID NO: 119 | RTYYRSRWFNDYAVS<br>K: SEQ ID NO: 120<br>I: SEQ ID NO: 120, res. 2-10<br>C: SEQ ID NO: 120 | ARGNMGAMDV<br>K: SEQ ID NO: 121, res 3-10<br>I: SEQ ID NO: 121<br>C: SEQ ID NO: 121 |
| B129 VH | GDRVSSNRAAWN<br>K: SEQ ID NO: 122, res 6-12<br>I: SEQ ID NO: 122, res. 1-10<br>C: SEQ ID NO: 122 | RTYYRSQWYNDYAVS<br>K: SEQ ID NO: 123<br>I: SEQ ID NO: 123, res. 2-10<br>C: SEQ ID NO: 123 | ARGTAMG-DA<br>K: SEQ ID NO: 124, res 3-9<br>I: SEQ ID NO: 124<br>C: SEQ ID NO: 124 |

-continued

| MAbs | HCDR1 | HCDR2 | HCDR3 |
|---|---|---|---|
| B139 VH | GDSVSSNSAAWN<br>K: SEQ ID NO: 125, res 6-12<br>I: SEQ ID NO: 125, res. 1-10<br>C: SEQ ID NO: 125 | RTYYRSKWYNDYAVS<br>K: SEQ ID NO: 126<br>I: SEQ ID NO: 126, res. 2-10<br>C: SEQ ID NO: 126 | ARQASNGFDI<br>K: SEQ ID NO: 127, res 3-10<br>I: SEQ ID NO: 127<br>C: SEQ ID NO: 127 |
| B172 VH | GDSVSSNSAAWN<br>K: SEQ ID NO: 128, res 6-12<br>I: SEQ ID NO: 128, res. 1-10<br>C: SEQ ID NO: 128 | RTYYRSKWYNDYAVS<br>K: SEQ ID NO: 129<br>I: SEQ ID NO: 129, res. 2-10<br>C: SEQ ID NO: 129 | ARQGTTGFDY<br>K: SEQ ID NO: 130, res 3-10<br>I: SEQ ID NO: 130<br>C: SEQ ID NO: 130 |

HCDRs of Antibodies Derived from A14 VL-Chain Shuffled Libraries

| MAbs | LCDR1 | HCDR2 | HCDR3 |
|---|---|---|---|
| #8 VL | SGSSSNIGNYYVSWY<br>K: SEQ ID NO: 131<br>I: SEQ ID NO: 131, res. 4-11<br>C: SEQ ID NO: 131 | DNAKRPS<br>K: SEQ ID NO: 132<br>I: SEQ ID NO: 132, res. 1-3<br>C: SEQ ID NO: 132 | QSYDNSLSGLV<br>K: SEQ ID NO: 133<br>I: SEQ ID NO: 133<br>C: SEQ ID NO: 133 |
| #20 VL | SGTSSNIGSKYVYWY<br>K: SEQ ID NO: 134<br>I: SEQ ID NO: 134, res. 4-11<br>C: SEQ ID NO: 134 | TNDQRPS<br>K: SEQ ID NO: 135<br>I: SEQ ID NO: 135, res. 1-3<br>C: SEQ ID NO: 135 | QSYDSSLRAVV<br>K: SEQ ID NO: 136<br>I: SEQ ID NO: 136<br>C: SEQ ID NO: 136 |
| #20-m1 VL | SGTSSNIGSFYVYWY<br>K: SEQ ID NO: 137<br>I: SEQ ID NO: 137, res. 4-11<br>C: SEQ ID NO: 137 | TNDQRPS<br>K: SEQ ID NO: 138<br>I: SEQ ID NO: 138, res. 1-3<br>C: SEQ ID NO: 138 | QSYDSSLRAVV<br>K: SEQ ID NO: 139<br>I: SEQ ID NO: 139<br>C: SEQ ID NO: 139 |
| #20-m2 VL | SGTSSNIGSFYVYWY<br>K: SEQ ID NO: 140<br>I: SEQ ID NO: 140, res. 4-11<br>C: SEQ ID NO: 140 | TNDQRPS<br>K: SEQ ID NO: 141<br>I: SEQ ID NO: 141, res. 1-3<br>C: SEQ ID NO: 141 | QSYDSSLRAVV<br>K: SEQ ID NO: 142<br>I: SEQ ID NO: 142<br>C: SEQ ID NO: 142 |
| #20-m3 VL | SGTSSNIGSYYVYWY<br>K: SEQ ID NO: 143<br>I: SEQ ID NO: 143, res. 4-11<br>C: SEQ ID NO: 143 | TNDQRPS<br>K: SEQ ID NO: 144<br>I: SEQ ID NO: 144, res. 1-3<br>C: SEQ ID NO: 144 | QSYDSSLRAVV<br>K: SEQ ID NO: 145<br>I: SEQ ID NO: 145<br>C: SEQ ID NO: 145 |

In embodiments the invention provides an antibody antigen binding domain comprising a heavy chain variable region (Vh) comprising a CDR1, CDR2 and CDR3 combination and a light chain variable region (Vl) comprising a CDR1, CDR2 and CDR3 combination, or comprising a heavy chain variable region (Vh) and/or a light chain variable region (Vl), selected from: m36, 71, 76, T47, m1Q, 2H5, m150; and 4, 31, 32, 69, A14, A21, B103, B129, B139, B172; and 8, 20, 20-m1, 20-m2, 20-m3.

In embodiments the antibody antigen binding domain specifically binds aa11-28 or aa19-25 of pre-S1.

The invention also provides antibodies, particularly monoclonal antibodies, and F(ab) or F(ab)2 comprising a subject binding domain.

The invention also provides novel polynucleotides such as cDNAs and expression vectors, encoding a subject antigen binding domain, and cells comprising such polynucleotides, and non-human animals comprising such cells. The polynucleotides may be operably linked to a heterologous transcription regulating sequence for expression, and may be incorporated into such vectors, cells, etc.

The invention provides methods of using the subject domains to treat HBV or HDV infection, or to induce antibody-dependent cell-mediated cytotoxicity (ADCC), comprising administering the domain to a person determined to have HBV or HDV infection, to have been exposed to HBV or HDV, to be at high risk for HBV or HDV exposure or infection, to be in need of Pre-S1 domain antagonism, or to be otherwise in need thereof. The invention further provides the use of subject compositions for the manufacture of a medicament for HBV or HDV infection, optionally in conjunction with a virus replication inhibitor.

The invention includes all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWING

FIG. 1. HBV neutralization by 10 antibodies from 2H5 VH-chain shuffled library selections.

DESCRIPTION OF PARTICULAR EMBODIMENTS OF THE INVENTION

Unless the context indicates otherwise, the term "antibody" is used in the broadest sense and specifically covers antibodies (including full length monoclonal antibodies) and antibody fragments so long as they recognize HBV/HDV Pre-S1 or otherwise inhibit HBV/HDV. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Natural and engineered antibody structures are well known in the art, e.g. Strohl et al., *Therapeutic antibody engineering: Current and future advances driving the strongest growth area in the pharmaceutical industry*, Woodhead Publishing Series in Biomedicine No. 11, October 2012; Holliger et al. Nature Biotechnol 23, 1126-1136 (2005); Chames et al. Br J Pharmacol. 2009 May; 157(2): 220-233.

Monoclonal antibodies (MAbs) may be obtained by methods known to those skilled in the art. See, for example Kohler et al (1975); U.S. Pat. No. 4,376,110; Ausubel et at (1987-1999); Harlow et al (1988); and Colligan et at (1993). The mAbs of the invention may be of any immunoglobulin class including IgG, IgM, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

A "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the invention.

A "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. The expression vector further comprises a promoter to drive the expression of the polypeptide within the cells. Suitable expression vectors may be plasmids derived, for example, from pBR322 or various pUC plasmids, which are commercially available. Other expression vectors may be derived from bacteriophage, phagemid, or cosmid expression vectors.

EXAMPLES

Human monoclonal antibodies block viral infection of hepatitis B and D virus Here we disclose human monoclonal antibodies that can block HDV and HBV viral infections. These antibodies were identified from a large phage display antibody library, which was established using peripheral blood mononuclear cells from 93 healthy donors. By selection and screening of the antibody library using pre-S1 domain of HBV envelope protein as a target, a panel of human monoclonal antibodies with neutralizing activities against HBV and HDV infections were identified. Among them, 2H5, showed best neutralizing activities against HBV and HDV infections. The co-crystal structure of 2H5 in complex with its target (8 amino acids of the Pre-S1 domain) was solved. By optimizing 2H5 by chain shuffling approach we developed even more potent neutralizing antibodies. These antibodies recognize similar epitope as 2H5 and the epitope is highly conserved among different genotypes of HBV. An exemplary antibody, A14 was tested in mice bearing humanized NTCP and provided complete protection of mice from HDV infection, and animal studies confirmed protection against HBV infection.

Antigen target: pre-S1 peptides. As antigen for selection we used two peptides derived from the pre-S1 domain of HBV. They were synthesized by Scilight-peptide (Beijing, China) at purity greater than 95%. NC36b: a peptide comprising of residues 4-38 of the pre-S1 domain of HBV L protein with a biotin modification at its C-terminus. m47b: a myristoylated lipopeptide comprising of amino acids 2-48 of pre-S1 domain with a biotin modification at the C-terminus and a myristoylation modification at the N-terminus.

```
Pre-S1(2-48)    GTNLSVPNPLGFFPDHQLDPAFGANSNNPDWDFNPNKDHWPEANQVG (SEQ ID NO: 146)
m47b            Myr-G..........................................K-Biotin
NC36b                   N..................................K-Biotin
```

Human Monoclonal Antibodies Against Pre-S1 Peptides were Generated Based on Phage Display Antibody Technology with Modifications [1, 2].

Phage display antibody library. A human non-immune scFv (Single-chain variable fragment) antibody library was constructed from peripheral blood mononuclear cells (PBMCs) of 93 healthy donors. The library has a size of a total of $1.1 \times 10^{10}$ members.

Selection and screening of phage antibody library. Phage particles expressing scFv on their surface (phage-scFv) were prepared from the library and used for selection of scFvs against the synthesized NC36b and m47b. The peptides were captured on streptavidin-conjugated magnetic M-280 Dynabeads® (Life Technologies) and then incubated with $5\times10^{12}$ phage particles prepared from the library, respectively. For each peptide, two rounds of selection were performed. For each round of selection, in order to obtain high affinity antibodies, the amount of peptides captured onto the magnetic beads was optimized and extensive washing steps were applied. In addition, to recover high affinity binders from the magnetic beads and increase the diversity of phage-scFvs recovered, two elution methods including peptide competition elution and conventional basic triethanolamine solution were used. Subsequently, a total of about 2000 single clones were picked and rescued to produce phage-scFvs in the bacterial culture supernatant, and screened for specific binding to m47b and/or NC36b by enzyme-linked immunosorbent assay (ELISA). Clones that bound to m47b and/or NC36b with values of optical density at 450 nm>1.0 were scored as positive, whereas negative clones gave values of <0.1. For m47b and/or NC36b specific binding clones, the genes of variable regions of heavy (VH) and light (VL) chain were sequenced and their corresponding amino acid sequences were aligned to eliminate repeated clones and identify antibodies with different sequence for further characterization. A total of 109 clones with unique sequence were identified.

Further characterization of the antibodies with unique antibody sequences to identify the best antibody candidate. The antibody clones with unique sequence were either produced as purified phage-scFv particles or converted to scFv-Fc minibodies or full-length human IgG1s, and then tested for their binding activities by ELISA, and HBV and HDV neutralization activities in cell cultures. By these assays, antibodies were ranked based on their binding activity and neutralization activity. The top antibody with the highest neutralization activity was chosen for further development.

Preparation of purified phage-scFvs for ELISA or neutralization assay. The phage-scFvs in the supernatant of 10-30 mL bacterial culture were precipitated by PEG/NaCL and then quantified by a spectrometer. Activities of different phage-scFvs for antigen binding or neutralizing viral infection were evaluated based on the dose-response of serial diluted phage-Abs that was normalized to the same concentration.

Preparation of scFv-Fc minibodies. ScFv encoding gene from the phage-scFv expressing vector was subcloned into an expression vector containing human IgG1 Fc fragment at C-terminus of the scFv. To produce scFv-Fc, 293F (Life Technologies) or 293T cells (ATCC) were transiently transfected with the scFv-Fc expression plasmid, 72 hours after transfection, the cell culture supernatant were harvested and scFv-Fc was purified by Protein A affinity chromatography (Protein A Sepharose CL-4B, GE Healthcare).

Preparation of full-length IgG1 antibody. The VH and VL coding sequence of a scFv were separately subcloned into antibody heavy chain (HC) expression vector and light chain (LC) expression vector. To make IgG1 antibody, 293F or 293T cells were transiently co-transfected with the two expression plasmids (HC+LC plasmids) at a 1:1 ratio. 72 hours after transfection, the cell culture supernatant were harvested for purification of IgG1 by Protein A affinity chromatography.

ELISA assay. 5 μg/mL of streptavidin (Sigma) in phosphate buffered saline (PBS) was coated in U-bottom 96-well plate (Nunc, MaxiSorp™), 100 μL per well, at 4° C. overnight or 37° C. for 1 hour. 2 μg/mL (370 nM) of m47b or NC36b peptides at 100 μL per well were then captured onto the plates by incubation at 30° C. for 0.5-1 hour. For phage-scFv based ELISA, serial diluted phage-scFvs in PBS containing 2% nonfat milk were added to each well at 100 μL per well. Specific bound phage-scFvs were detected by adding HRP-conjugated mouse anti-M13 antibody (GE Healthcare) and incubated for 30 mins at 30° C. In between each incubation step, the ELISA plate was washed for 6 times with PBST solution (0.05% Tween20 containing PBS) at 200 μL per well. Followed by HRP-conjugated antibody incubation, the ELISA signal was developed by incubating with TMB substrate (Sigma) for 5-10 mins at 30° C. and then stop the reaction with 2M $H_2SO_4$ at 25 μL per well. The absorbance at 450 nm was read by a microplate reader (Bio-Rad). For scFv-Fc or IgG1 based ELISA, the method was basically the same as described above for phage-scFvs except the bound antibodies were detected by HRP-conjugated mouse anti-human IgG Fc antibody (Sigma).

Preparation of HBV and HDV viruses. HBV and HDV were produced as previously described [3]. HDV. Briefly, a plasmid containing a head to tail trimer of 1.0×HDV cDNA of a genotype I virus (Genebank accession number: AF425644.1) under the control of a CMV promoter was constructed with de novo synthesized HDV cDNA for the production of HDV RNPs. A pUC18 plasmid containing nucleotide 2431-1990 of HBV (Genotype D, Genebank accession number: U95551.1), was used for expressing HBV envelope proteins under the control of endogenous HBV promoter. HDV virions were produced by transfection of the plasmids in Huh-7 as previously described by Sureau et al [4]. The transfected cell culture supernatant was harvested and directly used for HDV neutralization assay. HBV. HBV genotype B, C and D viruses were produced by transfection of Huh-7 cells with a plasmid containing 1.05 copies of HBV genome under the control of a CMV promoter. Genotype B or C HBV viruses were also from plasma of HBV patients.

HBV and HDV neutralization assays. The neutralization assays were performed as previously described [3, 5] with minor modifications. HepG2-hNTCP cells (a HepG2 cell line stably expressing HBV and HDV receptor hNTCP (human sodium taurocholate cotransporting polypeptide))

were used in these assays. HepG2-hNTCP cells were cultured in PMM medium [3] for 12-24 hours in a 48-well plate before viral infection. About 500 multiplicities of genome equivalents (mge) of HDV or 200 mge of HBV mixed with different forms of antibodies: phage-scFvs, scFv-Fc or IgG1 were inoculated with HepG2-hNTCP cells in the presence of 5% PEG8000 and incubated for 16 hours. Cells were then washed with medium for three times and maintained in PMM. Cell culture medium was changed with fresh PMM medium every 2-3 days. For HDV infection, at 7 days post infection (dpi), HDV infected cells were fixed with 100% methanol at room temperature for 10 min, intracellular delta antigen was stained with 5 µg/mL of FITC conjugated 4G5 (a mouse anti-HDV Delta antigen monoclonal antibody) and nuclear were stained with DAPI. Images were collected by a Fluorescence Microscope (Nikon). The neutralization activity against HDV was determined based on the stained Delta antigen amount and strength. For HBV infection, at dpi 3, 5 and 7, the culture supernatant were collected and tested for HBV secreted viral antigen HBsAg and/or HBeAg with commercial ELISA kits (Wantai, Beijing, China). The levels of HBeAg and/or HBsAg were used to evaluate HBV neutralization activity of the antibodies.

Through the above described ELISA and HBV neutralization assays we identified some top antibodies, which showed specific binding with NC36b as well as m47b and 47b (a peptide similar to m47b but without the myristoylation and showed neutralization activities in HBV.

Among these top antibodies, m36, 2H5 and m1Q were the top three antibodies showing best HBV (genotype D) neutralization activity. m36 was excluded from further testing as it showed reduced expression when converted into full-length IgG1. 2H5 and m1Q were further compared for HDV neutralization activity, 2H5 showed better activity in neutralizing HDV infection. Based on the high binding activity with the peptide and potent neutralizing activity against HBV and HDV, 2H5 was chosen for further development. In addition, 2H5 showed greater HBV and HDV neutralization activity than a previously published pre-S1 peptide antibody KR127 [6-8]. In HBV infection assay, 2H5-IgG1 is 11-fold more potent than KR127 as indicated by the $IC_{50}$ (the antibody concentration resulting 50% inhibition of HBV infection); 2H5 also showed greater inhibitory effect on HDV infection assay.

Mapping the binding epitope of 2H5 antibody. To map the epitope of 2H5 on pre-S1 region, we synthesized short peptides covering different regions of the pre-S1 domain and tested their ability to compete for the binding of 2H5 to m47b by competition ELISA assay. The shortest peptide that can compete for the binding is the LN16 peptide (corresponding to the NT amino acid (aa) 11-28 of the pre-S1 domain of HBV L protein (Genotype D), indicating the binding epitope of 2H5 is located within this region. LD15 and LA15 peptides also showed some degree of competition activity but at lower level than LN16. The common amino acids shared by the three peptides, LN16, LD15 and LA15, are aa19-25 of pre-S1. We therefore tested LN16 peptide each carrying a single alanine mutation at position 19, 20, 22 and 23, LN16-L19A, -D20A, -P21A, -F23A, for their competition activity, the result showed that all of them had reduced competition activity (LN16-L19A) or completely lost this activity (LN16-D20A, -P21A, -F23A), indicating these amino acids are critically important for pre-S1 binding to 2H5.

The 2H5 epitope is highly conserved among the majority of HBV genotypes. Sequence alignment of pre-S1 peptides of eight HBV genotypes showed that the epitope is highly conserved among them. The major variable amino acid is at position 24: glycine in genotype A and C, a lysine or arginine in genotype D and other genotypes. To test if this amino acid change will affect 2H5 binding to pre-S1 peptide, the NC36b peptide containing an arginine at position 24 was synthesized and test for binding with 2H5 by ELISA. The result showed that this amino acid change had only minimal effect on the binding. This is consistent with the HBV and HDV viral neutralization result that 2H5 neutralized HBV of genotype D and HDV carrying HBV genotype D envelopes.

Structural characterization of the 2H5 scFv and pre-S1 peptide complex. We also determined the crystal structure of 2H5 (as the scFv fragment fused with a $His_6$ tag at its N-terminal) in complex with a pre-S1 peptide, 59C. The amino acid sequence of 59C corresponds to aa-10-48 of pre-S1 of genotype C: GGWSSKPRQGMGTNLSVPNPL-GFFPDHQLDPAFGANSNNPDWDFNPNKDHW-PEANQV (SEQ ID NO:147). 2H5-scFv and 59C were co-expressed in $E.$ $coli$. The complex was purified as a complex by Immobilized Metal Ion Affinity Chromatography (IMAC) using Ni-NTA agarose beads (QIAGEN) followed by Size Exclusion Chromatography-HPLC (SEC-HPLC) with Superdex S200 10/300 column (GE Healthcare). The purified 2H5-scFv/59C complex was then concentrated and crystallized at 20° C. using the hanging-drop vapor-diffusion method by mixing 1 µL of protein (29 mg/mL in 10 mM Tris-HCl pH 8.0 and 100 mM NaCl) and 1 µL of reservoir solution containing 2.8 M sodium acetate, pH 7.0. Needle-shaped crystals appeared after 10 days. The X-ray diffraction data were collected at the Shanghai Synchrotron Radiation Facility beamline BL17U and processed by HKL2000 [9]. The structure was determined at 2.7 A° resolution by molecular replacement in Phaser [10, 11] using VH and VL derived from the structure of Herceptin-Fab complex (PDB 3H0T) [12] as starting model. Initial model from molecular replacement was further refined in Phenix [13] and manually rebuilt with Coot [14]. The final model includes 220 residues of 2H5 scFv, residues 20-27 of the 59C peptide. RAMPAGE analysis shows that 96.71% of residues are in the favored region and 3.29% of residues are in the allowed region [15]. The structure revealed that both VH and VL of 2H5 scFv participate in the interaction with the peptide. The eight amino acids of the peptide included in the structure are $D_{20}P_{21}A_{22}F_{23}G_{24}N_{25}A_{26}S_{27}$. Among them, $D_{20}$, $P_{21}$, $A_{22}$, $F_{23}$, $A_{26}$ and $S_{27}$ make interactions with 2H5. Three amino acids, $D_{20}$, $P_{21}$ and $F_{23}$ make critical interactions for 2H5 binding.

Improvement of 2H5 affinity and neutralization activity by VH-Chain shuffling.

Identification of four top antibodies from VH-chain shuffled library of 2H5. We next used chain shuffling to improve 2H5's binding affinity and neutralization activity, in which one of the two chains (VH and VL) is fixed and combined with a repertoire of the other chain to yield a secondary library that can be selected for superior activity. First, we did VH chain shuffling, in which VL of 2H5 was fixed and paired with a library of VH chains. Two VH-Lib/2H5VL phage display libraries were constructed. One library size is ~2×10$^8$, the other one is about 9×10$^8$. By using peptides captured on streptavidin-conjugated magnetic M-280 Dynabeads® (Life Technologies) as target, the two VH-Lib/2H5VL libraries were separately selected for one round each. At the end of the one round of selection from both libraries, total 576 individual clones were randomly picked and screened for binding with m47b by ELISA. Positive clones in ELISA were selected and sequenced. 10 clones with unique VH sequences (Table 1) and showed equal or stronger binding activity to m47$_b$ in phage antibody form than 2H5 were identified. These 10 clones were then converted into full-length human IgG1 and validated for binding to m47b by ELISA, neutralizing HBV (genotype D)

(FIG. 1) and HDV by in vitro neutralization assays. Four top antibodies, #31, #32, A14 and A21 were selected based on their overall activities in binding to m47b, neutralizing HBV and HDV.

TABLE 1

VH sequence alignment of 10 antibodies from 2H5 VH-chain shuffled library selections.

```
          QVQLQQSGPGLVKPSQTLSLTCAISGDSVSSNSAAWNWIRQSPSRGLEWLGRTYYRSKWY

#4   VH   ......................G........K.VT.....E..TG.............F
#31  VH   ............................................................
#32  VH   ............................................................
#69  VH   ...........M................SR.T.....E..TG.............F
2H5  VH   ......................G........K...........................H
A14  VH   ............................................................
A21  VH   ............................................................
B103 VH   ......................G........K..T...V...A...........R.F
B129 VH   ...........L................R...R.....V.................Q..
3172 VH   ............................................................
B139 VH   ................T...V.......................................

NDYAVSVKSRITINPDTSKNQFSLQLNSVTPEDTAVYYCARGKMGGMDVWGQGTTVTVSS
          (SEQ ID NO: 148)

#4   VH   ............V....................RG......A..................
#31  VH   .........................................T.QSWH..E..........
#32  VH   ..............S............K...........SIAT.T.Y.....L.....
#69  VH   ............V....................RG......A..................
2H5  VH   ........................................Q..AL...............
A14  VH   ........................................TRW.........L.....
A21  VH   ........................................A.VY.V.............
B103 VH   ...........VK................S.....I......N..A..............
B129 VH   ..........V...S..A....V................TAM.-.A....L.....
B172 VH   ........................................QGTT.F.Y..........
8139 VH   ......L.................................QASN.F.I....M.....
```

FIG. 1. shows HBV neutralization by 10 antibodies from 2H5 VH-chain shuffled library selections. HepG2-hNTCP cells were infected by incubation with HBV (genotype D) in the presence of antibodies at different concentrations for 16 hours. Antibody and viruses were washed away afterwards and continued to culture for 7 days, cell culture medium was changed every 2 days. The secreted HBeAg was detected by ELISA at 7 days post infection. Based on the reduction of HBeAg level, the HBV neutralization activity was calculated and expressed as the percentage changes for infected cells in the presence of antibodies relative to the control (cells infected in the presence of a control antibody).

Epitope mapping of the four top antibodies from 2H5 VH-chain shuffled libraries. As described above, we used peptide competition ELISA method to map the binding epitope of the four top antibodies identified from 2H5 VH-chain shuffled libraries. The LN16 peptide (corresponding to the NT amino acid (aa) 11-28 of pre-S1 domain), and LN16 peptide mutants, LN16-L19A, -D20A, -P21A, -F23A were used to compete for binding of these antibodies to m47b peptide. Our data revealed that all of them had similar peptide competition pattern as 2H5, amino acids, L19, D20, P21 and F23 are important for these antibodies' binding. The D20 and F23 are most important for all antibodies, whereas L19 and P21 played slightly variable role for different antibodies.

Further characterize the four top antibodies from 2H5 VH-chain shuffled libraries. These antibodies have more than 15-20 fold improved HBV (genotype D) neutralization activity as compared to the parental 2H5 antibody. The IC50 for these antibodies are around ~10-40 pM. A representative antibody out of these 4 antibodies, A14, was further compared to Hepatitis B Immune Globulin in neutralizing HBV (genotype D) infection. HBIG is prepared from the plasma of donors who have high antibody levels of the hepatitis B surface antigen (HBsAg) and used as a post exposure prophylaxis for people at risk to develop hepatitis B in clinic. A14 showed more than 1000-fold greater neutralization activity than HBIG. Furthermore, A14 showed broadly neutralization activity against other two HBV genotypes, B and C. The IC50 for genotype B, C and D are 80 pM, 30 pM and 10 pM, respectively. A14 was also examined for neutralizing six HBV genotype C viruses from plasma of HBV infected patients. Again A14 was at least several hundreds to 1000-fold more potent than HBIG in neutralizing these viruses.

A14 is the one with the highest Fab melting temperatures (Tm) of 80.2° C., reflecting the best thermostability of its variable domains. A14 is stabilized by approximately 2° C. comparing to the original 2H5, whereas other three nAbs all have slightly reduced thermostability. The thermostability was measured using differential scanning calorimetry (DSC).

Using primary human hepatocytes (PHH), we also demonstrated the potent neutralization activity of A14 against two HBV clinical strains from HBV patient plasma samples. One virus is genotype B; the other virus is a genotype C virus. HBsAg or HBeAg secreted to cell culture supernatants was examined every two days over the entire infection course using commercial kits (Autobio Diagnostics Co., Ltd.).

A14 competed with pre-S1 for binding to NTCP expressed on cells. A14 effectively competed with pre-S1 (FITC labeled pre-S1 peptide: m59) for binding to NTCP expressed on HepG2 cells in a dose-dependent manner.

A14 has no cross reactivity with 12 different cell lines representing 6 different tissues. This was analyzed by Western blotting and immunostaining assays.

A14 has antibody mediated cytotoxicity (ADCC) activity against cells carrying its epitope on cell surface and HBV producing cells as well as infected cells. In the ADCC assay, the epitope of A14 was stably expressed on CHO cell surface, HBV producing DE19 cells, and infected HepG2-hNTCP cells were used as target cells. A human NK cell line (NK92-MI expressing CD16 (V158 allele) and FcRgamma chain was used as effector cells. The effector cells and target cells (E/T) were co-cultured at a ratio of 6:1 for 6 hours in the presence of A14 or its Fc mutant. The cell killing was determined by using LDH release assay kit form Promega. The ADCC assay showed that A14 exhibited strong specific killing of CHO cells expressing the epitope, HBV producing cells, and HBV-infected HepG2-hNTCP cells but not the control cells lacking of the epitope expression, non-HBV producing cells and non-HBV infected cells. Meanwhile, the A14's Fc mutant (D265A/N297A) that lacks the ADCC activity but retains the same binding activity had no ADCC activity.

ADCC activity is common to antibodies having the same or similar epitope as A14, including 2H5, and its VH chain shuffled derived ones: 4, 31, 32, 69, A14, A21, B103, B129, B139, B172, and the VL chain shuffled clones #8, 20, 20-m1, 20-m2, 20-m3, and antibodies having distinct epitopes, such as m36, 71, 76, T47, m150, m1Q can also present ADCC activity; for example, m1Q, also showed ADCC activity, its epitope is approximate to the C-terminal of A14's epitope on preS1.

A14 protected mice from HDV infection. We previously revealed that the molecular determinant restricting mouse NTCP (mNTCP) to support viral entry of HBV and HDV is located within the residues 84-87 of mNTCP. When residues 84-87 were replaced by the human NTCP counterparts, it can effectively support viral infections in cell cultures [16]. Based on this, we have established a mouse model (background of FVB strain) that can support HDV infection by replacing mNTCP's residues at 84-87 with the corresponding residues of hNTCP using a genome editing method, TALEN [17, 18]. Using this mouse model, we tested if A14 can protect mice from HDV infection. FVB mice (age of 9 days after birth) with aa84-87 of mNTCP modified homozygotes were administered A14 mAb at 10 mg/kg of body weight. At 1 hour after mAb administration, mice were challenged with HDV viruses. At day 6 after HDV challenge, mice were sacrificed and liver tissues were harvested in liquid nitrogen immediately after collection. Mouse liver samples were then homogenized and lysed by Trizol® reagent to extract the total RNA. The RNA samples were reverse transcribed into cDNA with Prime Script RT-PCR Kit (Takara). To quantify HDV total RNA (genome equivalent) and edited NTCP RNA copies, the cDNA obtained from 20 ng RNA was used as template for real time PCR assay. Real time PCR was performed on an ABI Fast 7500 real time system instrument (Applied Biosystems, USA). The edited NTCP and HDV viral genome equivalent copies were calculated with a standard curve and the cellular GAPDH RNA was used as an internal control. A14 mAb completely blocked HDV infection, whereas HDV infection reached $1-10 \times 10^6$ copies/20 ng liver RNA in the control group. Mice in both groups had comparable NTCP rRNA copies in the liver tissue.

A14 Protected mice from HBV infection in a prophylaxis mouse model and inhibited HBV infection in a treatment mouse model. A mouse HBV infection model has been established using FRG (Fah–/–Rag2–/–/IL2rg–/–) triple knock-out mice transplanted with human hepatocytes [19, 20]. The FRG mice allows transplanted human hepatocytes replicating in mouse liver to form a chimeric liver with up to 98% human hepatocytes, as such the liver humanized FRG mice (FRGC) are highly susceptible to HBV infection. To test the prophylactic effect of A14, 10 FRGC mice were divided into two groups, five mice each. A14 prophylaxis group mice were injected with A14 at 15 mg/kg dosage by a single IP administration one day prior to HBV virus challenge, while mice in the control group were injected with same volume of PBS. On day 0, all mice were injected with 10e9 GE (genome equivalent) HBV each via tail vein. To test the therapeutic effect of A14, FRGC mice were challenged with 10e9 GE/mice of HBV via tail vein on day 0, on day 5 post-infection, the mice were treated with entecavir (ETV) control or A14 or HBIG. ETV was orally given at 0.1 mg/kg daily; A14 or HBIG were administrated every three days by I.P. injection at 20 mg/kg and 72 mg/kg (40 IU/kg), respectively. For both prophylaxis and treatment model, blood samples were collected every 3 days from all mice for measuring HBsAg and HBV DNA titer in serum. The mice were scarified at the end of the experiment, dpi35 and the liver tissues were preserved for immunohistochemical staining (IHC) of HBsAg and HBcAg. A14 showed 100% protection of FRGC mice from HBV infection in the prophylaxis model; it also showed significant inhibition of HBV infection in the treatment model.

Taken together, the results clearly demonstrated that A14 mAb is a potent HDV and HBV entry inhibitor in animal model. A14 mAb can be used to replace HBIG for prevention of HDV and HBV infection. On the other hand, A14 treatment of an established HBV infection in mice significantly inhibited HBV infection, moreover A14 showed specific ADCC activity against HBV-infected cells but not the non-HBV infected cells. These results indicate that A14 mAb may be combined with ETV to treat patient who are chronically infected by HBV. As A14 blocks new viral entry into host cells and has ADCC activity against infected cells, whereas ETV inhibits viral replication, combination of A14 with a viral replication inhibitor such as ETV, lamivudine, adefovir, tenofovir, telbivudine or other nucleoside and nucleotide analogues (NUCs) provide new therapeutic and prophylactic options for patients and can achieve better viremia control and HBsAg reduction.

Improvement of A14 affinity and neutralization activity by VL-Chain shuffling. To further improve A14 activity, we made an A14-VL chain shuffled phage display library, in which VH of A14 was fixed and paired with a library of VL chains. The final library (A14VH/VLlib) constructed had a size of ~$3\times10^8$. By using m47b peptide captured on streptavidin-conjugated magnetic M-280 Dynabeads® (Life Technologies) as target, the A14VH/VLlib library was selected for two rounds. 196 clones were screened for binding with m47b by ELISA. All clones were positive but 24 clones with highest OD450 reading were picked for sequencing. Two clones, #8 and #20, with different VL chain sequences than A14's VL were identified. These two antibodies were converted into full-length human IgG1 and tested for binding to m47b by ELISA. They both showed stronger binding activity to m47b than A14. In the HBV neutralization assay of HBV (genotype D), #8 showed 5-fold improvement in neutralizing HBV infection, whereas #20 showed similar activity as A14. Further mutagenesis of the VL of #20 (#20-m1, -m2, -m3) improved its neutralization activity by ~3-5-fold than A14, reached to the similar level as #8. The elevated HDV neutralization activities of these #20 mutants compared to A14 were demonstrated. Thus these A14-derived antibodies with further improved activities can be used similarly as A14 as described above, either alone or in combination with a viral replication inhibitor.

REFERENCES

1. Harrison, J. L., et al., *Screening of phage antibody libraries*. Methods Enzymol, 1996. 267: p. 83-109.

2. McCafferty, J., et al., *Phage antibodies: filamentous phage displaying antibody variable domains*. Nature, 1990. 348(6301): p. 552-4.

3. Yan, H., et al., *Sodium taurocholate cotransporting polypeptide is a functional receptor for human hepatitis B and D virus*. Elife, 2012. 1: p. e00049.

4. Sureau, C., et al., *Production of infectious hepatitis delta virus in vitro and neutralization with antibodies directed against hepatitis B virus pre-S antigens*. J Virol, 1992. 66(2): p. 1241-5.

5. Yan, H., et al., *Viral entry of hepatitis B and D viruses and bile salts transportation share common molecular determinants on sodium taurocholate cotransporting polypeptide*. J Virol, 2014. 88(6): p. 3273-84.

6. Hong, H. J., et al., *In vivo neutralization of hepatitis B virus infection by an anti-preS1 humanized antibody in chimpanzees*. Virology, 2004. 318(1): p. 134-41.

7. Ryu, C. J., et al., *Mouse monoclonal antibodies to hepatitis B virus preS1 produced after immunization with recombinant preS1 peptide*. Hybridoma, 2000. 19(2): p. 185-9.

8. Chi, S. W., et al., *Broadly neutralizing anti-hepatitis B virus antibody reveals a complementarity determining region H3 lid-opening mechanism*. Proc Natl Acad Sci USA, 2007. 104(22): p. 9230-5.

9. Otwinowski, Z. and W. Minor, *Processing of X-ray diffraction data collected in oscillation mode*. Methods Enzymol, 1997. 276: p. 307-326.

10. McCoy, A. J., et al., *Phaser crystallographic software*. J Appl Crystallogr, 2007. 40(Pt 4): p. 658-674.

11. McCoy, A. J., *Solving structures of protein complexes by molecular replacement with Phaser*. Acta Crystallogr D Biol Crystallogr, 2007. 63(Pt 1): p. 32-41.

12. Jordan, J. B., et al., *Hepcidin revisited, disulfide connectivity, dynamics, and structure*. J Biol Chem, 2009. 284(36): p. 24155-67.

13. Adams, P. D., et al., *PHENIX: a comprehensive Python-based system for macromolecular structure solution*. Acta Crystallogr D Biol Crystallogr, 2010. 66(Pt 2): p. 213-21.

14. Emsley, P. and K. Cowtan, *Coot: model-building tools for molecular graphics*. Acta Crystallogr D Biol Crystallogr, 2004. 60(Pt 12 Pt 1): p. 2126-32.

15. Lovell, S. C., et al., *Structure validation by Calpha geometry: phi,psi and Cbeta deviation*. Proteins, 2003. 50(3): p. 437-50.

16. Yan, H., et al., *Molecular determinants of hepatitis B and D virus entry restriction in mouse sodium taurocholate cotransporting polypeptide*. J Virol, 2013. 87(14): p. 7977-91.

17. Moscou, M. J. and A. J. Bogdanove, *A simple cipher governs DNA recognition by TAL effectors*. Science, 2009. 326(5959): p. 1501.

18. Boch, J., et al., *Breaking the code of DNA binding specificity of TAL-type III effectors*. Science, 2009. 326 (5959): p. 1509-12.

19. Strom, S. C., J. Davila, and M. Grompe, *Chimeric mice with humanized liver: tools for the study of drug metabolism, excretion, and toxicity*. Methods Mol Biol, 2010. 640: p. 491-509.

20. Bissig, K. D., et al., *Human liver chimeric mice provide a model for hepatitis B and C virus infection and treatment*. J Clin Invest, 2010. 120(3): p. 924-30.

Antibody sequences of 7 antibodies derived from naïve library m36 m36 VH DNA:

(SEQ ID NO: 01)

```
CAAGTTCCTTTATGTGCTGTCTCATCATTTTGGCAAGAATTCGCCACCAT

GAAACATCTGTGGTTCTTCCTTCTCCTGGTGGCAGCGGCCCAGCCGGCCA

TGGCCCAGATGCAGCTGGTGCAGTCTGGGGGAGGCTTGGTACAGCCTGGC

AGGTCCCTGAGACTCTCCTGTGCAGCCTCTGGATTCACCTTTGATGATTA

TGCCATGCACTGGGTCCGGCAAGCTCCAGGGAAGGGCCTGGAGTGGGTCT

CAGGTATTAGTTGGAATAGTGGTAGCATAGGCTATGCGGACTCTGTGAAG

GGCCGATTCACCATCTCCAGAGACAACGCCAAGAACTCCCTGTATCTGCA

AATGAACAGTCTGAGAGCTGAGGACACGGCCTTGTATTACTGTGCAAAAA

CGTCCTACGGGGGGGCTTTTGATATCTGGGGCCAAGGGACAATGGTCACC

GTCTCCTCA
``` m36 VL DNA:

(SEQ ID NO: 02)

```
CAGCCTGTGCTGACTCAATCGCCCTCAGCGTCTGGGACCCCCGGGCAGAG

GGTCACCATCTCTTGTTCTGGAAACACTTCCAACATCGGAAGTTATTATG

CATACTGGTATCAGCAACTCCCAGGAACGGCCCCCAAACTCCTCATCTAT
```

GATAATAATCAGCGGCCCTCGGGGATCCCTGCCCGATTCTCTGGCTCCAA

GTCTGGCACCTCAGCCTCCCTGGCCATCAGTGGGCTCCAGTCTGAGGATG

AGGCAGATTATTACTGTGCAACATGGGATGACAGCCTGAATGGTCCGGTG

TTCGGCGGAGGGACCAAGGTCACCGTCCTA m36 V14 Amino add:
(SEQ ID NO: 03)
QMQLVQSGCCLVQPCRSLRLSCAASGFTEDDYAMHWVRQAPCKCLEWVSG
ISWNSCSICYADSVKGRFTISRDNAKNSLYLQMNSLRAEDTALYYCAKTS
YCCAFDIWCQCTMVTVSS m36 V: Amino add:
(SEQ ID NO: 04)
QPVLTQSPSASGTPGQRVTISCSGNTSNIGSYYAYWYQQLPGTAPKLLIY
DNNQRPSGIPARFSGSKSGTSASLAISGLQSEDEADYYCATWDDSLNGPV
FGGGTKVTVL 71:
71 VH DNA:
(SEQ ID NO: 05)
CAGGTGCAGCTGGTGGAGTCTGGGGCTGAGGTGAAGAAGCCTGGGGCCTC

AGTGAAGGTCTCCTGCAAGGCTTCTGGATACACCTTCACCGGCTACTATA

TACATTGGGTGCGACAGGCCCCTGGACAAGGGCTTGAGTGGATGGGACGG

ATCAACCCTAACAGTGGTGGCACAAACTATGCACAGAAGTTTCAGGGCAG

GGTCACCATGACCAGGGACACGTCCATCAGGACGGCCTACATGGAACTGA

GTACACTGACATCTGACGACACGGCCGTTTATTACTGTGCGAGAGAAGGA

AGGGGCGGCATGGACGTCTGGGGCCAAGGGACCACGGTCACCGTCTCCTC

A

71 VL DNA:
(SEQ ID NO: 06)
GATGTTGTGATGACTCAGTCTCCACTCTCCCTGCCCGTCACCCCTGGAGA

GCCGGCCTCCATCTCCTGCAGGTCTAGTCAGAGCCTCCTGCATAGTAATG

GATACAACTATTTGGATTGGTACCTGCAGAAGCCAGGGCAGTCTCCACAG

CTCCTGATCTATTTGGGTTCTAATCGGGCCTCCGGGGTCCCTCACAGGTT

CACTCCCACTCCATCACGCACACATTTTACACTGAAAATCACCACAGTGG

AGCCTCACCATGTTCCCATTTATTACTGCATGCAACCTCTACAACCTCCC

ATCACCTTCCGCCACGCCACACGACTGGAGATTAAA

71 VH Amino add:
(SEQ ID NO: 07)
QVQLVESGAEVKKPGASVKVSCKASGYTFTGYYIHWVRQAPGQGLEWMGR
INPNSGGTNYAQKFQGRVTMTRDTSIRTAYMELSTLTSDDTAVYYCAREG
RGGMDVWGQGTTVTVSS 71 VL Amino acid:
(SEQ ID NO: 08)
DVVMTQSPLSLPVTPGEPASISCRSSQSLLHSNGYNYLDWYLQKPGQSPQ
LLIYLGSNRASGVPDRFSGSGSGTDFTLKISRVEAEDVGIYYCMQGLQPP
ITFGQGTRLEIK 76:
76 VH DNA:
(SEQ ID NO: 09)
GAGGTGCAGCTGTTGGAGACCGGGGGAGGCGTGGTCCAGCCTGGGAGGTC

CCTGAGACTCTCCTGTGCAGCCTCTGGATTCACCTTCAGTAGCTATGCTA

TGCACTGGGTCCGCCAGGCTCCAGGCAAGGGGCTGGAGTGGGTGGCAGTT

ATATCATATGATGGAAGCAATAAATACTACGCAGACTCCGTGAACCGCCG

ATTCACCATCTCCAGAGACAATTCCAAGAACACCCTCTATCTCCAAATGA

ACACCCTCAGACCTGACCACACCCCTCTCTATTACTGTCCGACTCGTCCT

TTTCATATCTGCGCCCAACCGACAATGGTCACCGTCTCTTCA

76 VL DNA:
(SEQ ID NO: 10)
GATGTTGTGATGACTCAGTCTCCACTCTCCCTGCCCGTCACCCTTGGACA

GCCGGCCTCCATCTCCTGCAGGTCTAGTCACAGCCTCGTATACAGTGATG

GAAACACCTACTTGAGTTGGTTTCACCAGAGGCCAGGCCAATCTCCAAGG

CGCCTAATTTATAAGGTTTCTAATCGGGACTTTGGGGTCCCAGACAGATT

CAGCGGCAGTGGGTCAGGCACTGACTTCACACTGAAGATCAGCAGGGTGG

AGGCTGAGGATGTTGGAGTTTATTACTGCATGCAAGGTACACACTGGCCT

GGGACGTTCGGCCAGGGGACCAAACTGGATATCAAA

76VHAmnoacid:
(SEQ ID NO: 11)
EVQLLETGGGVVQPGRSLRLSCAASGFTFSSYAMHWVRQAPGKGLEWVAV
ISYDGSNKYYADSVKGRFTISRDNSKNTLYLQMNSLRAEDTAVYYCASGA
FDIWGQGTMVTVSS 76VL Amino acid:
(SEQ ID NO: 12)
DVVMTQSPLSLPVTLGQPASISCRSSHSLVYSDGNTYLSWFHQRPGQSPR
RLIYKVSNRDFGVPDRFSGSGSGTDFTLKISRVEAEDVGVYYCMQGTHWP
GTFGQGTKLDIK T47:
T47 VH DNA:
(SEQ ID NO: 13)
CAGGTACAGCTGCAGCAGTCAGGTCCAGGACTGGTGAAGCCCTCGCAGAC

CCTCTCACTCTCCTGTGCCATCTCCGGGGACAGTGTCTCCAGCAACAGTG

TTGCTTGGAACTGGATCAGGCAGTCCCCATCGAGAGGCCTTGAGTGGCTG

GGAAGGACATACTACAGGTCCAAGTGGTATAATGATTATGCAGTCTCTGT

GAAAAGTCGAATAACCATCAACCCAGACACATCCAAGAACCAGTTCTCCC

TGCAGCTGAGCTCTGTGACTCCCGAGGACACGGCTGTATATTACTGTGCA

AGAGCCGATGGTTCGCGAGGGGAGGGTATGACCAGTGGGGCCAGGGAAC

CCTGGTCACCGTCTCTTCA

T47 VL DNA:
(SEQ ID NO: 14)
GACATCGTGATGACCCAGTCTCCAGACTCCCTGGCTGTGTCTCTGGGCGA

GAGGGCCACCATCAAATGCAAGTCCAGTCAGTCTATTTTATACAGGTCCA

ACAATAAGAACTACTTAGCTTGGTACCAACACAAACCAGGACAGCCTCCT

AAGCTGCTCATTTCCTGGGCATCTACCCGGGAATCCGGGGTCCCTGACCG

ATTCAGTGGCAGCGGGTCTGGGACAGATTTCACTCTCACCATCAACAGCC

TGCAGGCTGAAGATGTGGCGGTTTATTACTGTCAGCAATATTATACTACT

CCTCAGACTTTTGGCCAGGGGACCAAGGTGGAGATCAAA

T47 VH Amino acid:
(SEQ ID NO: 15)
QVQLQQSGPGLVKPSQTLSLSCAISGDSVSSNSVAWNWIRQSPSRGLEWL
GRTYYRSKWYNDYAVSVKSRITINPDTKNQFSLQLSSVTPEDTAVYYCA
RADGSRGGGYDQWGQGTLVTVSS T47 VL Amino acid:
(SEQ ID NO: 16)
DIVMTQSDDSLAVSLGERATIKCKSSQSILYRSNNKNYLAWYQHKPGQDD
KLLISWASTRESGVDDRFSCSGSCTDFTLTINSLQAEDVAVYYCQQYYTT
DQTFGQGTKVEIK m1Q
m1Q VH DNA
(SEQ ID NO: 17)

```
CAGGTCCAGTTGGTGGAGTCTGGGGGAGGCGTGGTCCAGCCTGGGAGGTC

CCTGAGACTCTCCTGTGCAGCCTCTGGATTCACCTTCAGTAGCTATGCTA

TGCACTGGGTCCGCCAGGCTCCAGGCAAGGGGCTGGAGCAGGTGGCAGTT

ATATCATATGATGGAAGTAATAAATACTACGTAGACTCCGTGAAGGGCCG

ATTCACCATCTCCAGAGACAATTCCAAGAACACGCTGTATCTGCAAATGA

ACAGCCTGAGAGCTGAGGACACGGCTGTGTATTACTGTGCGAGATCTACA

TACGGTATGGACGTCTGGGGCCAAGGGACCACGGTCACCGTCTCCTCA
``` m1Q-VL DNA
(SEQ ID NO: 18)
```
GATGTTGTGATGACTCAGTCTCCACTCTCCCTGCCCGTCACCCTTGGACA

GTCGGCCTCCATCTCCTGCACGTCTACTCAAAGCCTCGTACACAGTCATG

GAAACACCTACTTGAATTGCTTTCACCAGAGGCCAGGCCAATCTCCAAGG

CGCCTAATTTATAAGGTTTCTAATCGGGACTCCGGGGTCCCAGACAGATT

CAGCGGCAGTGGGTCACACACTCATTTCACACTCCAAATCACCACCGTGC

AGGCCCACGATCTTGGCATTTATTACTCCATGCAAGGTACACACTGGTCC

ACCTTCGCCCAAGCCACCAAGCTGGATATCAAA
``` m1Q VH Amino acid:
(SEQ ID NO: 19)
QVQLVESGGGVVQPGRSLRLSCAASGFTFSSYAMHWVRQAPGKGLEQVAV
ISYDGSNKYYVDSVKGRFTISRDNSKNTLYLQMNSLRAEDTAVYYCARST
YGMDVWGQGTTVTVSS m10Q Vk Amino acid:
(SEQ ID NO: 20)
DVVMTQSPLSLPVTLGQSASISCRSSQSLVHSDGNTYLNWFQQRPGQSPR
RLIYKVSNRDSGVPDRFSGSGSDTDFTLEISRVEAEDVGIYYCMQGTHWW
TFGQGTKLDIK 2H5:
2H5 VH DNA:
(SEQ ID NO: 21)
```
CAGGTACAGCTGCAGCAGTCAGGTCCAGGACTGGTGAAGCCCTCGCAGAC

CCTCTCACTCACCTGTGGCATCTCCGGGGACAGTGTCTCTAGCAAGAGTG

CTGCTTGGAACTGGATCAGGCAGTCCCCTTCGAGAGGCCTTGAGTGGCTG

GGAAGGACATACTACAGGTCCAAGTGGCATAATGATTATGCAGTATCTGT

GAAAAGTCGAATAACCATCAACCCAGACACATCCAAGAACCAGTTTTCCC

TGCAGCTGAACTCTGTGACCCCCGAAGACACGGCTGTGTATTATTGTGCG

CGCGGCCAGATGGGAGCTTTGACGTCTGGGGCCAAGGGACCACGGTCAC

CGTCTCCTCA
```

2H5 VL DNA:
(SEQ ID NO: 22)
```
CAGTCTGTGTTGACGCAGCCGCCCTCAGCGTCTGGGACCCCCGGGCAGAG

GGTCACCATCTCTTGTTCTGGAAGCAGCTCCAACATCGGAAGTTATTATG

TATACTGGTACCAGCAATTCCCAGGAACGGCCCCCAAACTCCTCATCTAT

GGTAATAATCAGCGGCCCTCAGGGGTCCCTGACCGATTCTCTGGCTCCAA

GTCTGGCACCTCAGCCTCCCTGGCCATCACTGGGCTCCAGGCTGAGGATG

AGGCTGATTATTACTGTCAGTCCTATGACAGCAGCCTGAGTGGTGTGATA

TTCGGCGGAGGGACCAAGCTGACCGTCCTA
```

2H5 VH Amino acid:
(SEQ ID NO: 23)
QVQLQQSGPGLVKPSQTLSLTCGISGDSVSSKSAAWNWIRQSPSRGLEWL
GRTYYRSKWHNDYAVSVKSRITINPDTSKNQFSLQLNSVTPEDTAVYYCA
RGQMGALDVWGQGTTVTVSS 2H5 VL Amino acid:
(SEQ ID NO: 24)
QSVLTQPPSASGTPGQRVTISCSGSSSNIGSYYVYWYQQFPGTAPKLLIY
GNNQRPSGVPDRFSGSKSGTSASLAITGLQAEDEADYYCQSYDSSLSGVI
FGGGTKLTVL m150
m150 VH DNA:
(SEQ ID NO: 25)
```
GAGGTGCAGCTGGTGCAGTCTGGGGGAGGCGTGGTCCAGCCTGGGAGGTC

CCTGAGACTCTCCTGTGCAGCCTCTGGATTCACCTTCAGTAGCTATGCTA

TGCACTGGGTCCGCCAGGCTCCAGGCAAGGGGCTGGAGTGGGTGGCAGTT

ATATCATATGATGGAAGTAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCTGTGTATTACTGTGCGAGGTTGGTG

GCTGGTCGAAGTGCTTTTGATATCTGGGGCCAAGGGACCACGGTCACCGT

CTCCTCA
``` m150 VK DNA:
(SEQ ID NO: 26)
```
GAAATTGTGCTGACTCAGTCTCCAGCCACCCTGTCTGTGTCTCCAGGGGA

AAGAGCCACCCTCTCCTGCAGGGCCAGTCAGAGTGTTAGCAGCAACTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGTATAATAACTGGCCTCCGATCACCTTCGGC

CAAGGGACACGACTGGAGATTAAA
``` m150 VH Amino acid:
(SEQ ID NO: 27)
EVQLVQSGGGVVQPGRSLRLSCAASGFIFSSYAMHWVRQAPGKGLEWVAV
ISYDGSNKYYADSVKGRFTISRDNSKNTLYLQMNSLRAEDTAVYYCARLV
AGRSAFDIWGQGTTVTVSS m150 VK Amino acid:
(SEQ ID NO: 28)
EIVLTQSPATLSVSPGERATLSCRASQSVSSNLAWYQQKPGQAPRLLIYG
ASTRATGIPARFSGSGSGTEFILTISSLQSEDFAVYYCQQYNNWPPITEG
QGTRLEIK Antibody sequences of 10 antibodies derived from 2H5 VH-chain shuffled library selection. Note, these antibodies have the same VL sequence as 2H5, therefore only VH sequences of these antibodies were listed below.

4
4 VH DNA:
(SEQ ID NO: 29)
```
CAGGTACAGCTGCAGCAGTCAGGTCCAGGACTGGTGAAGCCCTCGCAGACCCTCTCACTCACCT

GTGGCATCTCCGGGGACAGTGTCTCTAGCAAGAGTGTTACTTGGAACTGGATCAGGGAGTCTCC
```

-continued

AACGGGAGGCCTTGAGTGGCTGGGCAGGACATACTATAGGTCCAAGTGGTTTAATGATTATGCA

GTATCTGTGAAAAGTCGAATAACTGTCAACCCAGACACATCCAAGAACCAGTTTTCCCTGCAGC

TAAACTCTGTGACTCCCGAGGACAGGGGTGTCTATTACTGCGCACGCGCCAAGATGGGAGGTAT

GGACGTCTGGGGCCAGGGGACCACGGTCACCGTCTCTTCA

4 VH Amino Acid:
(SEQ ID NO: 30)

QVQLQQSGPGLVKPSQTLSLICGISGDSVSSKSVTWNWIRESPIGGLEWLGRTYYRSKWFNDYA
VSVKSRITVNPDTSKNQFSLQLNSVTPEDRGVYYCARAKMGGMDVWGQGTTVTVSS

31 VH DNA:
(SEQ ID NO: 31)

CAGGTACAGCTGCAGCAGTCAGGTCCAGGACTGGTGAAGCCCTCGCAGACCCTCTCACTCACCT

GTGCCATCTCCGGGGACAGTGTCTCTAGCAACAGTGCTGCTTGGAACTGGATCAGGCAGTCCCC

ATCGAGAGGCCTTGAGTGGCTGGGAAGGACATACTACAGGTCCAAGTGGTATAATGATTATGCA

GTATCTGTGAAAAGTCGAATAACCATCAACCCAGACACATCCAAGAACCAGTTCTCCCTGCAGC

TCAACTCTCTGACTCCCCACCACACGCCTCTTTATTACTCTACAACACACACTTGCCACGCTAT

CCAAGTCTCCCCCCAACCCACCACCGTCACCCTCTCCTCA

31 VH Amino acid:
(SEQ ID NO: 32)

QVQLQQSGPGLVKPSQTLSLTCAISGDSVSSNSAAWNWIRQSPSRGLEWLGRTYYRSKWYNDYA
VSVKSRITINPDTSKNQFSLQLNSVTPEDTAVYYCTRQSWHGMEVWGQGTTVTVSS

32 VH DNA:
(SEQ ID NO: 33)

CAGGTACAGCTGCAGCAGTCAGGTCCAGGACTGGTGAAGCCCTCGCAGACCCTCTCACTCACCT

GTGCCATCTCCGGGGACAGTGTCTCTAGCAACAGTGCTGCTTGGAACTGGATCAGGCAGTCCCC

ATCGAGAGGCCTTGAGTGGCTGGGAAGGACATACTACAGGTCCAAGTGGTATAATGATTATGCA

GTATCTGTGAAAAGTCGAATAACCATCAACTCAGACACATCGAAGAACCAGTTCTCCCTGCAGC

TGAAGTCTGTGACTCCCGAGGACACGGCTGTGTATTACTGTGCAAGGAGTATAGCAACAGGTAC

TGACTACTGGGGCCAGGGAACCCTGGTCACCGTCTCCTCA

32 VH Amino acid:
(SEQ ID NO: 34)

QVQLQQSGPCLVKPSQTLSLTCAISGDSVSSNSAAWNWIRQSPSRCLEWLCRTYYRSKWYNDYA
VSVKSRITINSDTSKNQFSLQLKSVTPEDTAVYYCARSIATGTDYWGQGTLVTVSS

69 VH DNA:
(SEQ ID NO: 35)

CAGGTACAGCTGCAGCAGTCAGGTCCAGGACTGATGAAGCCCTCGCAGACCCTCTCACTCACCT

GTGCCATCTCCGGGGACAGTGTCTCTAGTAGCCGTGCTACTTGGAACTGGATCAGGGAGTCTCC

AACGGGAGGCCTTGAGTGGCTGGGCAGGACATACTATAGGTCCAAGTGGTTTAATGATTATGCA

GTATCTGTGAAAAGTCGAATAACTGTCAACCCAGACACATCCAAGAACCAGTTTTCCCTGCAGC

TAAACTCTGTGACTCCCGAGGACAGGGGTGTCTATTACTGCGCACGCGCCAAGATGGGAGGTAT

GGACGTCTGGGGCCAGGGGACCACGGTCACCGTCTCCTCA

69 VH Amino acid:
(SEQ ID NO: 36)

QVQLQQSGPGLMKPSQTLSLICAISGDSVSSSRATWNWIRESPIGGLEWLGRTYYRSKWFNDYA
VSVKSRITVNPDTSKNQFSLQLNSVIPEDRGVYYCARAKMGGMDVWGQGTTVTVSS

A14 VH DNA:
(SEQ ID NO: 37)

CAGGTACAGCTGCAGCAGTCAGGTCCAGGACTGGTGAAGCCCTCGCAGACCCTCTCACTCACCT

CTCCCATCTCCCCCCACACTCTCTCTACCAACAGTCCTCCTTCCAACTCCATCAGCCACTCCCC

ATCGAGAGGCCTTGAGTGGCTGGGAAGGACATACTACAGGTCCAAGTGGTATAATGATTATGCA

GTATCTGTGAAAAGTCGAATAACCATCAACCCAGACACATCCAAGAACCAGTTCTCCCTGCAGC

-continued

```
TGAACTCTGTGACTCCCGAGGACACGGCTGTGTATTACTGTGCAAGAGGAACACGTTGGGGTAT

GGACGTCTGGGGCCAAGGGACCCTGGTCACTGTCTCCTCA
```

A14 VH Amino acid:

(SEQ ID NO: 38)

QVQLQQSGPGLVKPSQTLSLTCAISGDSVSSNSAAWNWIRQSFSRGLEWLGRTYYRSKWYNDYA
VSVKSRITINFDTSKNQFSLQLNSVTFEDTAVYYCARGTRWGMDVWGQGTLVTVSS

A21 VH DNA:

(SEQ ID NO: 39)

```
CAGGTACAGCTGCAGCAGTCAGGTCCAGGACTGGTGAAGCCCTCGCAGACCCTCTCACTCACCT

GTGCCATCTCCGGGGACAGTGTCTCTAGCAACAGTGCTGCTTGGAACTGGATCAGGCAGTCCCC

ATCGAGAGGCCTTGAGTGGCTGGGAAGGACATACTACAGGTCCAAGTGGTATAATGATTATGCA

GTATCTGTGAAAAGTCGAATAACCATCAACCCAGACACATCCAAGAACCAGTTCTCCCTGCAGC

TGAACTCTGTGACTCCCGAGGACACGGCTGTGTATTACTGTGCAAGAGCGAAAGTGTACGGTGT

GGACGTCTGGGGCCAAGGGACCACGGTCACCGTCTCCTCA
```

A21 VH Amino acid:

(SEQ ID NO: 40)

QVQLQQSGPGLVKPSQTLSLTCAISGDSVSSNSAAWNWIRQSFSRGLEWLGRTYYRSKWYNDYA
VSVKSRITINFDTSKNQFSLQLNSVTFEDTAVYYCARAKVYGVDVWGQGTTVTVSS

B103 VH DNA:

(SEQ ID NO: 41)

```
CAGGTACAGCTGCAGCAGTCAGGTCCAGGACTGGTGAAGCCCTCGCAGACCCTCTCACTCACCT

GTGGCATCTCCGGGGACAGTGTCTCTAGCAAGAGTGCCACTTGGAACTGGGTCAGGCAGTCCGC

ATCGAGAGGCCTTGAGTGGCTGGGAAGGACATACTACAGGTCCAGGTGGTTTAATGATTATGCA

GTGTCTGTGAAAAGTCGAATAACCGTCAAGCCAGACACATCCAAGAACCAGTTTTCCCTGCAAT

TAAATTCTGTGAGTCCCGAGGACACGGCTATCTATTACTGTGCACGCGGCAACATGGGAGCTAT

GGACGTCTGGGGCCAAGGGACCACGGTCACCGTCTCTTCA
```

B103 VH Amino acid:

(SEQ ID NO: 42)

QVQLQQSGPGLVKPSQTESLICGISGDSVSSKSATWNWVRQSASRGLEWLGRTYYRSRWFNDYA
VSVKSRITVKPDTSKNQFSLQLNSVSPEDTAIYYCARGNMGAMDVWGQGTTVTVSS

B129 VH DNA:

(SEQ ID NO: 43)

```
CAGGTACAGCTGCAGCAGTCAGGTCCAGGACTGCTGAAGCCCTCGCAGACCCTCTCACTCACCT

GTGCCATCTCCGGGGACAGGGTCTCTAGCAATAGAGCTGCTTGGAACTGGGTCAGGCAGTCCCC

ATCGAGAGGCCTTGAGTGGCTGGGAAGGACATACTACAGGTCCCAGTGGTATAATGATTATGCA

GTCTCTGTAAAAAGTCGAGTGACCATCAGCCCAGACGCATCCAAGAACCAAGTCTCCCTGCAGC

TGAACTCTGTGACTCCCGAGGACACGGCTGTGTATTACTGTGCAAGAGGTACAGCTATGGGTGA

CGCCTGGGGCCAGGGAACCCTGGTCACCGTCTCTTCA
```

B129 VH Amino acid:

(SEQ ID NO: 44)

QVQLQQSGPGLLKPSQTLSLTCAISGDRVSSNRAAWNWVRQSPSRGLEWLGRTYYRSQWYNDYA
VSVKSRVTISPDASKNQVSLQLNSVTPEDTAVYYCARGTAMGDAWGQGTLVTVSS

B139 VH DNA:

(SEQ ID NO: 45)

```
CAGGTACAGCTGCAGCAGTCAGGTCCAGGACTGGTGAAGCCCTCGCAGACCCTCACACTCACCT

GTGTCATCTCCGGGGACAGTGTCTCTAGCAACAGTGCTGCTTGGAACTGGATCAGGCAGTCCCC

ATCCACAGCCCTTCAGTCCCTCCCAACCACATACTACACCTCCAACTCCTATAATCATTATCCA

CTTTCTCTCAAAACTCCAATAACCATCAACCCAGACACATCCAACAACCACTTCTCCCTGCAGC

TGAACTCTGTGACTCCCGAGGACACGGCTGTGTATTACTGTGCAAGACAAGCCTCCAACGGTTT

TGATATCTGGGGCCAAGGGACAATGGTCACCGTCTCTTCA
```

B139 VH Amino acid:
(SEQ ID NO: 46)

QVQLQQSGPGLVKPSQTLTLTCVISGDSVSSNSAAWNWIRQSPSRGLEWLGRTYYRSKWYNDYA
VSLKSRITINPDTSKNQFSLQLNSVTPEDTAVYYCARQASNGFDIWGQGTMVTVSS

B172 VH DNA:
(SEQ ID NO: 47)

CAGGTACAGCTGCAGCAGTCAGGTCCAGGACTGGTGAAGCCCTCGCAGACCCTCTCACTCACCT

GTGCCATCTCCGGGGACAGTGTCTCTAGCAACAGTGCTGCTTGGAACTGGATCAGGCAGTCCCC

ATCGAGAGGCCTTGAGTGGCTGGGAAGGACATACTACAGGTCCAAGTGGTATAATGATTATGCA

GTATCTGTGAAAAGTCGAATAACCATCAACCCAGACACATCCAAGAACCAGTTCTCCCTGCAGC

TGAACTCTGTGACTCCCGAGGACACGGCTGTGTATTACTGTGCAAGACAGGGGACGACAGGCTT

TGACTACTGGGGCCAGGGAACCACGGTCACCGTCTCCTCA

B172 VH Amino acid:
(SEQ ID NO: 48)

QVQLQQSGPCLVKPSQTLSLTCAISCDSVSSNSAAWNWIRQSPSRCLEWLCRTYYRSKWYNDYA
VSVKSRITINPDTSKNQFSLQLNSVTPEDTAVYYCARQGTTGFDYWGQGTTVTVSS

Antibody sequences of two antibodies derived from A14 VL-chain shuffled library
selection. Note, these antibodies have the same VH sequence as A14, there-
fore only VL
sequences of these two antibodies were listed below.

8 VL DNA:
(SEQ ID NO: 49)

CAGTCTGTCGTGACGCAGCCGCCCTCAGTGTCTGCGGCCCCAGGACAGAAGGTCACCATCTCCT

GCTCTGGAAGCAGCTCCAACATTGGGAATTATTATGTGTCCTGGTACCAGCACCTCCCAGGAAC

AGCCCCCAAACTCCTCATTTATGACAATGCTAAGCGACCCTCAGGGATTCCTGACCGATTCTCT

GGCTCCAAGTCTGGCACGTCAGCCACCCTGGGCATCACTGGGCTCCGGGCTGAGGATGAGGCTG

ATTATTACTGCCAGTCCTATGACAATAGCCTTAGTGGTTTGGTGTTCGGCGGAGGGACCAAGCT

GACCGTCCTA

8 VL amino acid:
(SEQ ID NO: 50)

QSVVTQPPSVSAAPCQKVTISCSCSSSNICNYYVSWYQHLPCTAPKLLIYDNAKRPSCIPDRFS
GSKSGTSATLGITGLRAEDEADYYCQSYDNSLSGLVFGGGTKLTVL

20 VL DNA:
(SEQ ID NO: 51)

CAGTCTGTGTTGACGCAGCCACCCTCAGCGTCTGGGACCCCCGGGCAGAGGGTCACCATCTCTT

GTTCTGGAACCAGCTCCAACATCGGAAGTAAGTATGTATACTGGTACCAGCGGCTCCCAGGAAC

GGCCCCCAAACTCCTCATCTATACTAATGATCAGCGGCCCTCAGGGGTCCCTGCCCGATTCTCT

GGCTCCAAGTCTGGCACCTCAGCCTCCCTGGCCATCACTGGGCTCCAGGCTGAGGATGAGGCTG

ATTATTACTGCCAGTCCTATGACAGCAGCCTGCGTGCTGTGGTTTTCGGCGGAGGGACCAAGCT

GACCGTCCTA

20 VL amino acid:
(SEQ ID NO: 52)

QSVLTQPPSASGTPGQRVTISCSGTSSNIGSKYVYWYQRLPGTAPKLLIYTNDQRPSGVPARFS
GSKSGTSASLAITGLQAEDEADYYCQSYDSSLRAVVFGGGTKLTVL

20-ml VL DNA:
(SEQ ID NO: 53)

CAGTCTGTGTTGACGCAGCCACCCTCAGCGTCTGGGACCCCCGGGCAGAGGGTCACCATCTCTT

GTTCTGGAACCAGCTCCAACATCGGAAGTTTCTATGTATACTGGTACCAGCGGCTCCCAGGAAC

GGCCCCCAAACTCCTCATCTATACTAATGATCAGCGGCCCTCAGGGGTCCCTGCCCGATTCTCT

CGCTCCAACTCTGCCACCTCACCCTCCCTCCCCATCACTCCGCTCCAGGCTCAGGATCAGCCTC

ATTATTACTCCCACTCCTATCACACCACCCTCCGTCCTCTCCTTTTCCGCCCAGGCACCAACCT

GACCGTCCTA

-continued

20-m1 VL amino acid:
(SEQ ID NO: 54)

QSVLTQPPSASGTPGQRVTISCSGTSSNIGSFYVYWYQRLPGTAPKLLIYTNDQRPSGVPARFS
GSKSGTSASLAITGLQAEDEADYYCQSYDSSLRAVVFGGGTKLTVL

20-m2 VL DNA:
(SEQ ID NO: 55)

CAGTCTGTGTTGACGCAGCCACCCTCAGCGTCTGGGACCCCCGGGCAGAGGGTCACCATCTCTT

GTTCTGGAACCAGCTCCAACATCGGAAGTTTCTATGTATACTGGTACCAGCAGCTCCCAGGAAC

GGCCCCCAAACTCCTCATCTATACTAATGATCAGCGGCCCTCAGGGGTCCCTGCCCGATTCTCT

GGCTCCAAGTCTGGCACCTCAGCCTCCCTGGCCATCACTGGGCTCCAGGCTGAGGATGAGGCTG

ATTATTACTGCCAGTCCTATGACAGCAGCCTGCGTGCTGTGGTTTTCGGCGGAGGGACCAAGCT

GACCGTCCTA

20-m2 VL amino acid:
(SEQ ID NO: 56)

QSVLTQPPSASGTPGQRVTISCSGTSSNIGSFYVYWYQQLPGTAPKLLIYTNDQRPSGVPARFS
GSKSGTSASLAITGLQAEDEADYYCQSYDSSLRAVVFGGGTKLTVL

20-m3 VL DNA:
(SEQ ID NO: 57)

CAGTCTGTGTTGACGCAGCCACCCTCAGCGTCTGGGACCCCCGGGCAGAGGGTCACCATCTCTT

GTTCTGGAACCAGCTCCAACATCGGAAGTTACTATGTATACTGGTACCAGCAGCTCCCAGGAAC

GGCCCCCAAACTCCTCATCTATACTAATGATCAGCGGCCCTCAGGGGTCCCTGCCCGATTCTCT

GGCTCCAAGTCTGGCACCTCAGCCTCCCTGGCCATCACTGGGCTCCAGGCTGAGGATGAGGCTG

ATTATTACTGCCAGTCCTATGACAGCAGCCTGCGTGCTGTGGTTTTCGGCGGAGGGACCAAGCT

GACCGTCCTA

20-m3 VL amino acid:
(SEQ ID NO: 58)

QSVLTQPPSASGTPGQRVTISCSGTSSNIGSYYVYWYQQLPGTAPKLLIYTNDQRPSGVPARFS
GSKSGTSASLAITGLQAEDEADYYCQSYDSSLRAVVFGGGTKLTVL

What is claimed is:

1. An antibody, or antigen-binding fragment thereof that specifically binds HBV to the Pre-S1 domain of Hepatitis B virus (HBV) surface antigen, and wherein the antibody, or antigen-binding fragment thereof comprises:

a) a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;

b) a heavy chain variable region CDR1 comprising amino acids having the sequence set forth in residues 6-12 of SEQ ID NO: 89, a heavy chain variable region CDR2 comprising amino acids having the sequence set forth in SEQ ID NO: 90, and a heavy chain variable region CDR3 comprising amino acids having the sequence set forth in residues 3-10 of SEQ ID NO: 91; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;

c) a heavy chain variable region CDR1 comprising amino acids having the sequence set forth in residues 6-10 of SEQ ID NO: 59, a heavy chain variable region CDR2 comprising amino acids having the sequence set forth in SEQ ID NO: 60, and a heavy chain variable region CDR3 comprising amino acids having the sequence set forth in residues 3-11 of SEQ ID NO: 61; and a light chain variable region CDR1 comprising amino acids having the sequence set forth in SEQ ID NO: 62, a light chain variable region CDR2 comprising amino acids having the sequence set forth in SEQ ID NO: 63, and a light chain variable region CDR3 comprising amino acids having the sequence set forth in SEQ ID NO: 64, utilizing Kabat system;

d) a heavy chain variable region CDR1 comprising amino acids having the sequence set forth in residues 5-9 of SEQ ID NO: 65, a heavy chain variable region CDR2 comprising amino acids having the sequence set forth in SEQ ID NO: 66, and a heavy chain variable region CDR3 comprising amino acids having the sequence set forth in residues 3-10 of SEQ ID NO: 67; and a light chain variable region CDR1 comprising amino acids having the sequence set forth in residues 1-12 of SEQ ID NO: 68, a light chain variable region CDR2 comprising amino acids having the sequence set forth in SEQ ID NO: 69, and a light chain variable region CDR3 comprising amino acids having the sequence set forth in SEQ ID NO: 70, utilizing Kabat system;

e) a heavy chain variable region CDR1 comprising amino acids having the sequence set forth in residues 6-10 of SEQ ID NO: 71, a heavy chain variable region CDR2 comprising amino acids having the sequence set forth in SEQ ID NO: 72, and a heavy chain variable region CDR3 comprising amino acids having the sequence set forth in residues 3-7 of SEQ ID NO: 73; and a light chain variable region CDR1 comprising amino acids having the sequence set forth in SEQ ID NO: 74, a light chain variable region CDR2 comprising amino acids having the sequence set forth in SEQ ID NO: 75, and a light chain variable region CDR3 comprising amino acids having the sequence set forth in SEQ ID NO: 76, utilizing Kabat system;

f) a heavy chain variable region CDR1 comprising amino acids having the sequence set forth in residues 6-12 of SEQ ID NO: 77, a heavy chain variable region CDR2 comprising amino acids having the sequence set forth in SEQ ID NO: 78, and a heavy chain variable region CDR3 comprising amino acids having the sequence set forth in residues 3-13 of SEQ ID NO: 79; and a light chain variable region CDR1 comprising amino acids having the sequence set forth in SEQ ID NO: 80, a light chain variable region CDR2 comprising amino acids having the sequence set forth in SEQ ID NO: 81, and a light chain variable region CDR3 comprising amino acids having the sequence set forth in SEQ ID NO: 82, utilizing Kabat system;
g) a heavy chain variable region CDR1 comprising amino acids having the sequence set forth in residues 6-10 of SEQ ID NO: 83, a heavy chain variable region CDR2 comprising amino acids having the sequence set forth in SEQ ID NO: 84, and a heavy chain variable region CDR3 comprising amino acids having the sequence set forth in residues 3-9 of SEQ ID NO: 85; and a light chain variable region CDR1 comprising amino acids having the sequence set forth in SEQ ID NO: 86, a light chain variable region CDR2 comprising amino acids having the sequence set forth in SEQ ID NO: 87, and a light chain variable region CDR3 comprising amino acids having the sequence set forth in SEQ ID NO: 88, utilizing Kabat system;
h) a heavy chain variable region CDR1 comprising amino acids having the sequence set forth in residues 6-10 of SEQ ID NO: 95, a heavy chain variable region CDR2 comprising amino acids having the sequence set forth in SEQ ID NO: 96, and a heavy chain variable region CDR3 comprising amino acids having the sequence set forth in residues 3-12 of SEQ ID NO: 97; and a light chain variable region CDR1 comprising amino acids having the sequence set forth in SEQ ID NO: 98, a light chain variable region CDR2 comprising amino acids having the sequence set forth in SEQ ID NO: 99, and a light chain variable region CDR3 comprising amino acids having the sequence set forth in SEQ ID NO: 100, utilizing Kabat system;
i) a heavy chain variable region CDR1 comprising amino acids having the sequence set forth in residues 6-12 of SEQ ID NO: 101, a heavy chain variable region CDR2 comprising amino acids having the sequence set forth in SEQ ID NO: 102, and a heavy chain variable region CDR3 comprising amino acids having the sequence set forth in residues 3-10 of SEQ ID NO: 103; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
j) a heavy chain variable region CDR1 comprising amino acids having the sequence set forth in residues 6-12 of SEQ ID NO: 104, a heavy chain variable region CDR2 comprising amino acids having the sequence set forth in SEQ ID NO: 105, and a heavy chain variable region CDR3 comprising amino acids having the sequence set forth in residues 3-10 of SEQ ID NO: 106; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
k) a heavy chain variable region CDR1 comprising amino acids having the sequence set forth in residues 6-12 of SEQ ID NO: 107, a heavy chain variable region CDR2 comprising amino acids having the sequence set forth in SEQ ID NO: 108, and a heavy chain variable region CDR3 comprising amino acids having the sequence set forth in residues 3-10 of SEQ ID NO: 109; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
l) a heavy chain variable region CDR1 comprising amino acids having the sequence set forth in residues 6-12 of SEQ ID NO: 110, a heavy chain variable region CDR2 comprising amino acids having the sequence set forth in SEQ ID NO: 111, and a heavy chain variable region CDR3 comprising amino acids having the sequence set forth in residues 3-10 of SEQ ID NO: 112; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
m) a heavy chain variable region CDR1 comprising amino acids having the sequence set forth in residues 6-12 of SEQ ID NO: 116, a heavy chain variable region CDR2 comprising amino acids having the sequence set forth in SEQ ID NO: 117, and a heavy chain variable region CDR3 comprising amino acids having the sequence set forth in residues 3-10 of SEQ ID NO: 118; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
n) a heavy chain variable region CDR1 comprising amino acids having the sequence set forth in residues 6-12 of SEQ ID NO: 119, a heavy chain variable region CDR2 comprising amino acids having the sequence set forth in SEQ ID NO: 120, and a heavy chain variable region CDR3 comprising amino acids having the sequence set forth in residues 3-10 of SEQ ID NO: 121; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
o) a heavy chain variable region CDR1 comprising amino acids having the sequence set forth in residues 6-12 of SEQ ID NO: 122, a heavy chain variable region CDR2 comprising amino acids having the sequence set forth in SEQ ID NO: 123, and a heavy chain variable region CDR3 comprising amino acids having the sequence set forth in residues 3-9 of SEQ ID NO: 124; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;
p) a heavy chain variable region CDR1 comprising amino acids having the sequence set forth in residues 6-12 of SEQ ID NO: 125, a heavy chain variable region CDR2 comprising amino acids having the sequence set forth in SEQ ID NO: 126, and a heavy chain variable region CDR3 comprising amino acids having the sequence set forth in residues 3-10 of SEQ ID NO: 127; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;

q) a heavy chain variable region CDR1 comprising amino acids having the sequence set forth in residues 6-12 of SEQ ID NO: 128, a heavy chain variable region CDR2 comprising amino acids having the sequence set forth in SEQ ID NO: 129, and a heavy chain variable region CDR3 comprising amino acids having the sequence set forth in residues 3-10 of SEQ ID NO: 130; and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94, utilizing Kabat system;

r) a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115; and a light chain variable region CDR1 comprising amino acids having the sequence set forth in SEQ ID NO: 131, a light chain variable region CDR2 comprising amino acids having the sequence set forth in SEQ ID NO: 132, and a light chain variable region CDR3 comprising amino acids having the sequence set forth in SEQ ID NO: 133, utilizing Kabat system;

s) a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115; and a light chain variable region CDR1 comprising amino acids having the sequence set forth in SEQ ID NO: 134, a light chain variable region CDR2 comprising amino acids having the sequence set forth in SEQ ID NO: 135, and a light chain variable region CDR3 comprising amino acids having the sequence set forth in SEQ ID NO: 136, utilizing Kabat system;

t) a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115; and a light chain variable region CDR1 comprising amino acids having the sequence set forth in SEQ ID NO: 137, a light chain variable region CDR2 comprising amino acids having the sequence set forth in SEQ ID NO: 138, and a light chain variable region CDR3 comprising amino acids having the sequence set forth in SEQ ID NO: 139, utilizing Kabat system;

u) a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115; and a light chain variable region CDR1 comprising amino acids having the sequence set forth in SEQ ID NO: 140, a light chain variable region CDR2 comprising amino acids having the sequence set forth in SEQ ID NO: 141, and a light chain variable region CDR3 comprising amino acids having the sequence set forth in SEQ ID NO: 142, utilizing Kabat system; or v) a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115; and a light chain variable region CDR1 comprising amino acids having the sequence set forth in SEQ ID NO: 143, a light chain variable region CDR2 comprising amino acids having the sequence set forth in SEQ ID NO: 144, and a light chain variable region CDR3 comprising amino acids having the sequence set forth in SEQ ID NO: 145, utilizing Kabat system.

2. The antibody, or antigen-binding fragment thereof of claim 1, comprising a heavy chain variable region CDR1 comprising amino acids having the sequence set forth in residues 6-12 of SEQ ID NO: 113, a heavy chain variable region CDR2 comprising amino acids having the sequence set forth in SEQ ID NO: 114, and a heavy chain variable region CDR3 comprising amino acids having the sequence set forth in residues 3-10 of SEQ ID NO: 115, and a light chain variable region CDR1 comprising amino acids having the sequence set forth in SEQ ID NO: 92, a light chain variable region CDR2 comprising amino acids having the sequence set forth in SEQ ID NO: 93, and a light chain variable region CDR3 comprising amino acids having the sequence set forth in SEQ ID NO: 94.

3. The antibody, or antigen-binding fragment thereof, of claim 1, wherein the antibody or antigen-binding fragment thereof further comprises a Fc domain.

4. The antibody, or antigen-binding fragment thereof, of claim 1, wherein the antibody or antigen-binding fragment thereof exhibits antibody-dependent cell-mediated cytotoxicity (ADCC) activity in an ADCC assay.

5. The antibody, or antigen-binding fragment thereof, of claim 1, wherein the antibody is a monoclonal antibody.

6. The antibody, or antigen-binding fragment thereof, of claim 5, wherein the antibody is a human monoclonal antibody.

7. A method of treating or preventing Hepatitis B virus (HBV) or Hepatitis D virus (HDV) infection in a subject, comprising administering to the subject the antibody or antigen-binding fragment thereof of claim 1, wherein the subject is determined to have HBV or HDV infection or has been exposed to HBV or HDV.

8. The method of claim 7, wherein the antibody or antigen-binding fragment thereof is administered by injection.

* * * * *

UNITED STATES PATENT AND TRADEMARK OFFICE
CERTIFICATE OF CORRECTION

PATENT NO. : 10,544,205 B2
APPLICATION NO. : 15/864494
DATED : January 28, 2020
INVENTOR(S) : Sui et al.

It is certified that error appears in the above-identified patent and that said Letters Patent is hereby corrected as shown below:

In the Claims

At Claim 1, Column 93, Line 27, please replace "binds HBV to the Pre-S1" with --binds to the Pre-S1--.

Signed and Sealed this
Tenth Day of August, 2021

Drew Hirshfeld
*Performing the Functions and Duties of the
Under Secretary of Commerce for Intellectual Property and
Director of the United States Patent and Trademark Office*